(12) United States Patent
Reihsen et al.

(10) Patent No.: US 9,805,624 B2
(45) Date of Patent: Oct. 31, 2017

(54) SIMULATED, REPRESENTATIVE HIGH-FIDELITY ORGANOSILICATE TISSUE MODELS

(71) Applicant: Regents of the University of Minnesota, Minneapolis, MN (US)

(72) Inventors: Troy E. Reihsen, St. Paul, MN (US); Robert M. Sweet, Edina, MN (US); Daniel M. Burke, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 13/630,715

(22) Filed: Sep. 28, 2012

(65) Prior Publication Data

US 2013/0085736 A1 Apr. 4, 2013

Related U.S. Application Data

(60) Provisional application No. 61/541,547, filed on Sep. 30, 2011, provisional application No. 61/589,463, filed on Jan. 23, 2012, provisional application No. 61/642,117, filed on May 3, 2012.

(51) Int. Cl.
| | |
|---|---|
| *G09B 23/28* | (2006.01) |
| *G09B 23/30* | (2006.01) |
| *G06F 19/00* | (2011.01) |
| *B33Y 50/00* | (2015.01) |
| *B33Y 80/00* | (2015.01) |

(52) U.S. Cl.
CPC ......... *G09B 23/30* (2013.01); *G06F 19/3437* (2013.01); *G09B 23/28* (2013.01); *B33Y 50/00* (2014.12); *B33Y 80/00* (2014.12)

(58) Field of Classification Search
CPC .. G06G 7/60; G06F 17/30; B32B 3/26; B05D 3/02
See application file for complete search history.

(56) References Cited

U.S. PATENT DOCUMENTS

| | | | |
|---|---|---|---|
| 6,428,323 | B1 | 8/2002 | Pugh |
| 2004/0002642 | A1 | 1/2004 | Dekel et al. |
| 2007/0003749 | A1* | 1/2007 | Asgari ................. 428/304.4 |
| 2008/0208549 | A1* | 8/2008 | Gaved et al. ............. 703/11 |
| 2010/0168763 | A1 | 7/2010 | Zhao et al. |
| 2010/0248200 | A1 | 9/2010 | Ladak et al. |

FOREIGN PATENT DOCUMENTS

| | | |
|---|---|---|
| GB | 2212371 A | 7/1989 |
| WO | WO-2011067707 A2 | 6/2011 |
| WO | WO-2011150257 A2 | 12/2011 |
| WO | WO-2013165529 A2 | 11/2013 |
| WO | WO-2013165529 A3 | 11/2013 |

OTHER PUBLICATIONS

Hutmacher, "Scaffold design and fabrication technologies for engineering tissues—state of the art and future perspectives," J. Biomater. Sci., Polymer Edn., vol. 12, pp. 107-124, 2001.*
Moroni, "3D fiber-deposited scaffolds for tissue engineering: Influence of pores geometry and architecture on dynamic mechanical properties," Biomaterials, vol. 27, pp. 974-985, 2006.*
Berfield, "Fluorescent Image Correlation for Nanoscale Deformation Measurements," Small, vol. 2, pp. 631-635, 2006.*
Santra, "Synthesis and Characterization of Fluorescent, Radio-Opaque, and Paramagnetic Silica Nanoparticles for Multimodal Bioimaging Applications," vol. 17, pp. 2165, 2005.*
Stevens, "A Review of Materials, Fabrication Methods, and Strategies Used to Enhance Bone Regeneration in Engineered Bone Tissues," J Biomed Mater Res Part B: Appl Biomater, vol. 85B, p. 573-582, 2007.*
Kerdok, "Truth cube: Establishing physical standards for soft tissue simulation," Medical Image Analysis, vol. 7, p. 283-291, 2003.*
Kunkler, Kevin, et al., "Integrated Sensor Technology into Synthetic Anatomical Training", SITIS—SBIR/STTR Interactive Topic Information System, (Apr. 27, 2012).
"International Application Serial No. PCT/US2013/026933, International Search Report dated Dec. 19, 2013", 6 pgs.
"International Application Serial No. PCT/US2013/026933, Invitation to Pay Additional Fees and Partial Search Report dated Sep. 27, 2013", 5 pgs.
"International Application Serial No. PCT/US2013/026933, Written Opinion dated Dec. 19, 2013", 7 pgs.
"International Application Serial No. PCT/US2013/026933, International Preliminary Report on Patentability dated Nov. 13. 2014", 9 pgs.

* cited by examiner

*Primary Examiner* — G. Steven Vanni
(74) *Attorney, Agent, or Firm* — Schwegman Lundberg & Woessner, P.A.

(57) ABSTRACT

A method of making a tissue model comprises determining one or more material properties of a tissue, wherein the one or more material properties include at least one of mechanical properties, electroconductive properties, optical properties, thermoconductive properties, chemical properties, and anisotropic properties, creating an anatomical structure of the tissue, selecting an artificial tissue material having one or more material properties that substantially correspond to the one or more material properties of the tissue, and coupling the artificial tissue material to the anatomical structure.

30 Claims, 14 Drawing Sheets
(14 of 14 Drawing Sheet(s) Filed in Color)

SIMULATED, REPRESENTATIVE HIGH-FIDELITY ORGANOSILICATE TISSUE MODELS

CROSS-REFERENCE TO RELATED APPLICATIONS

The subject matter of this application is related to Reihsen et al., U.S. Provisional Patent Application Ser. No. 61/541,547, entitled "SIMULATED, REPRESENTATIVE HIGH-FIDELITY ORGANOSILICATE TISSUE MODELS," filed on Sep. 30, 2011, to Reihsen et al., U.S. Provisional Patent Application Ser. No. 61/589,463, entitled "SIMULATED, REPRESENTATIVE HIGH-FIDELITY ORGANOSILICATE TISSUE MODELS," filed on Jan. 23, 2012, and to Poniatowski et al., U.S. Provisional Patent Application Ser. No. 61/642,117, entitled "METHOD FOR ANALYZING SURGICAL TECHNIQUE USING ASSESSMENT MARKERS AND IMAGE ANALYSIS," filed on May 3, 2012, which are each incorporated by reference herein in their entirety.

TECHNICAL FIELD

The present disclosure is directed to models used for simulation of tissues, such as tissue models useful for providing training of medical procedures for health care providers, and in particular to human tissue models constructed with a base of organosilicates. The present disclosure also relates to a method of forming the models.

BACKGROUND ON THE INVENTION

Simulation of medical procedures is becoming a more prominent part of medical training. Currently, animal tissues are often used for simulation but are often anatomically different than a human patient, have different mechanical properties than human tissue with large amounts of variance between samples, are difficult to obtain and store, and have ethical issues regarding animal protection. Fresh, frozen, and fixed human cadaveric tissue is also used for medical education and device development, and training and offers better anatomical accuracy compared to animal tissue. However, human cadaveric tissue often still has different mechanical properties than live human tissue, is typically expensive, and is difficult to obtain and store in sufficient quantities for medical training. Cadaveric tissue also lacks the constitutive properties of fresh or live human tissue. Neither animal tissues nor cadaveric tissues meet the fidelity needs for enhanced training, and in some cases their deficiencies can lead to negative training transfer.

SUMMARY OF THE INVENTION

The present disclosure is directed to silicone-based simulation materials and methods for making the same that can be used to simulate tissue, such as human and animal tissue. The simulation tissue can be used for training medical or veterinary practitioners with a high-fidelity representative tissue model that will closely and accurately simulate patient tissue. In some examples, the tissue model can be patient-specific and designed for a particular individual so that the practitioner can perform a practice run of a procedure before actually working on the patient. In an example, the tissue simulation material comprises organo silicate materials.

In one example, the present disclosure is directed to a method of making a tissue model. The method can include determining one or more material properties of a tissue, wherein the one or more material properties include at least one of mechanical properties, electroconductive properties, optical properties, thermoconductive properties, chemical properties, and anisotropic properties, creating an anatomical structure of the tissue, selecting an artificial tissue material having one or more material properties that substantially correspond to the one or more material properties of the tissue, and coupling the artificial tissue material to the anatomical structure.

In another example, the present disclosure is directed to a tissue model comprising a three-dimensional model and an artificial tissue material coupled to the three-dimensional printed model. The artificial tissue material is selected to have one or more material properties that substantially corresponding to at least one of mechanical properties, electroconductive properties, optical properties, thermoconductive properties, chemical properties, and anisotropic properties of a tissue.

In yet another example, the present disclosure is directed to a tissue model comprising a three-dimensional model, an artificial tissue material coupled to the three-dimensional printed model, wherein the artificial tissue material is selected to have one or more material properties that substantially correspond to one or more material properties of a tissue, and an indicator material applied to the artificial tissue material.

BRIEF DESCRIPTION OF THE DRAWINGS

The patent or application file contains at least one drawing executed in color. Copies of this patent or patent application publication with color drawings will be provided by the Office upon request and payment of the necessary fee.

DETAILED DESCRIPTION OF THE INVENTION

The present disclosure is directed to silicone-based simulation materials and methods for making the same that can be used to simulate tissue, such as human or animal tissue. The simulation tissue can be used for training medical or veterinary practitioners with a high-fidelity representative tissue model that will closely and accurately simulate patient tissue. In some examples, the tissue model can be patient-specific and designed for a particular individual so that the practitioner can perform a practice run of a procedure before actually working on the patient.

As described above, animal tissue models and frozen human cadaveric tissue can be used to simulate human tissue. However, fidelity issues with animal and cadaveric tissue, as well as high cost and ethical issues often make animal tissue and cadaveric tissue models a poor simulation for living tissue. The factors that contribute to the variation in constitutive properties amongst fresh or live human tissue have been hypothesized but poorly documented. Fresh human tissue models are logistically difficult to obtain, store, process and lack embedded assessment methods for formative and summative feedback.

The discrepancies between current simulator materials and actual human tissue can lead to reduced efficacy when the trainee moves from simulation to actual patient care. Training on inaccurate and unrealistic models has the potential for negative training transfer. Even if the training model material provides a good model for live tissue generally, differences in a particular patient can still provide for training difficulties that are preferably experienced on non-living tissue. Therefore, efforts have been made toward developing tissue models that can be a functional analogue of living tissue. In some examples, patient-specific tissue models with representative mechanical physiology based on tissue elasticity and modulus can be made.

Figure 1:
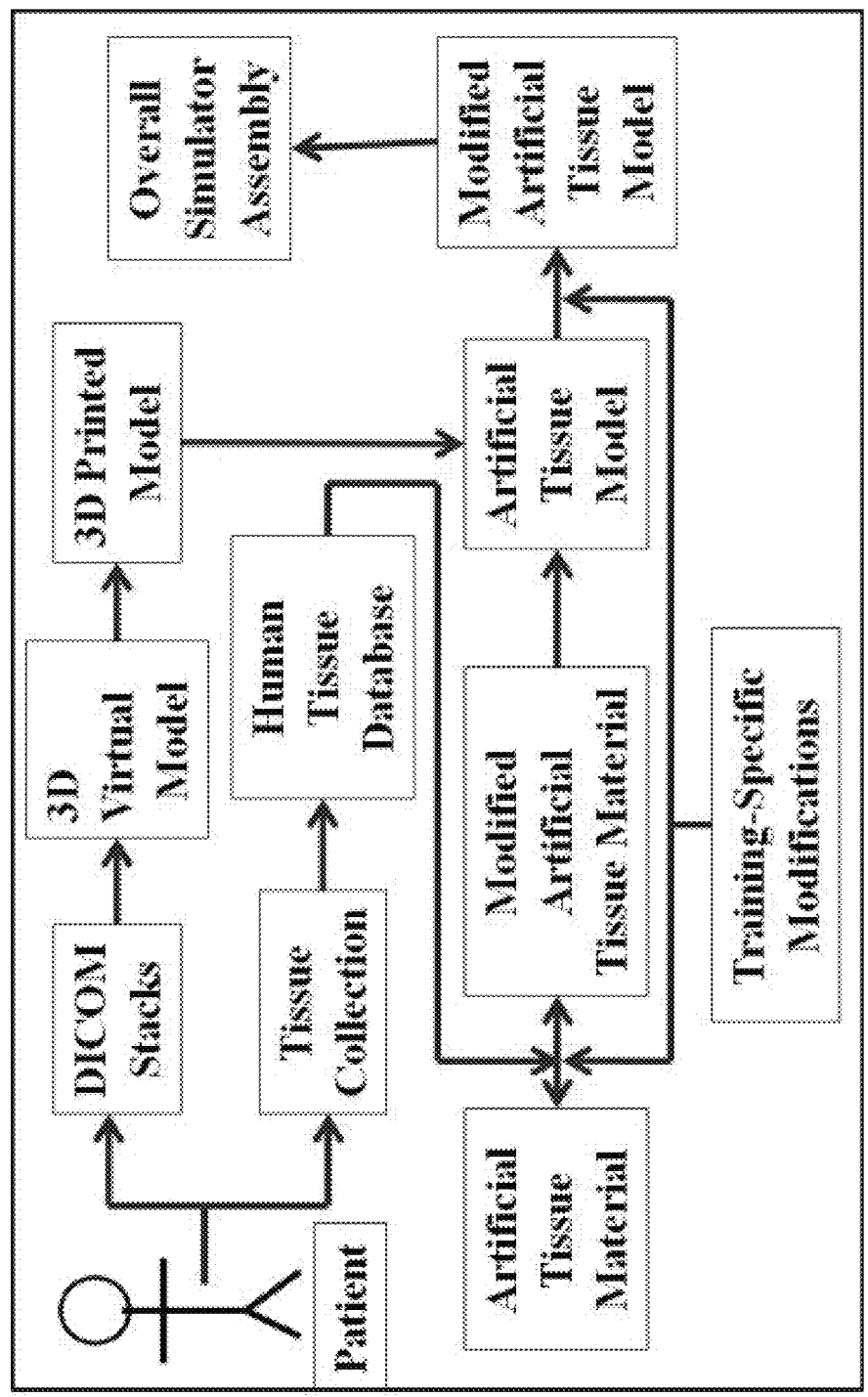
FIG. 1 is a flow diagram illustrating a method for creating desired artificial tissue models.
Figure 2:
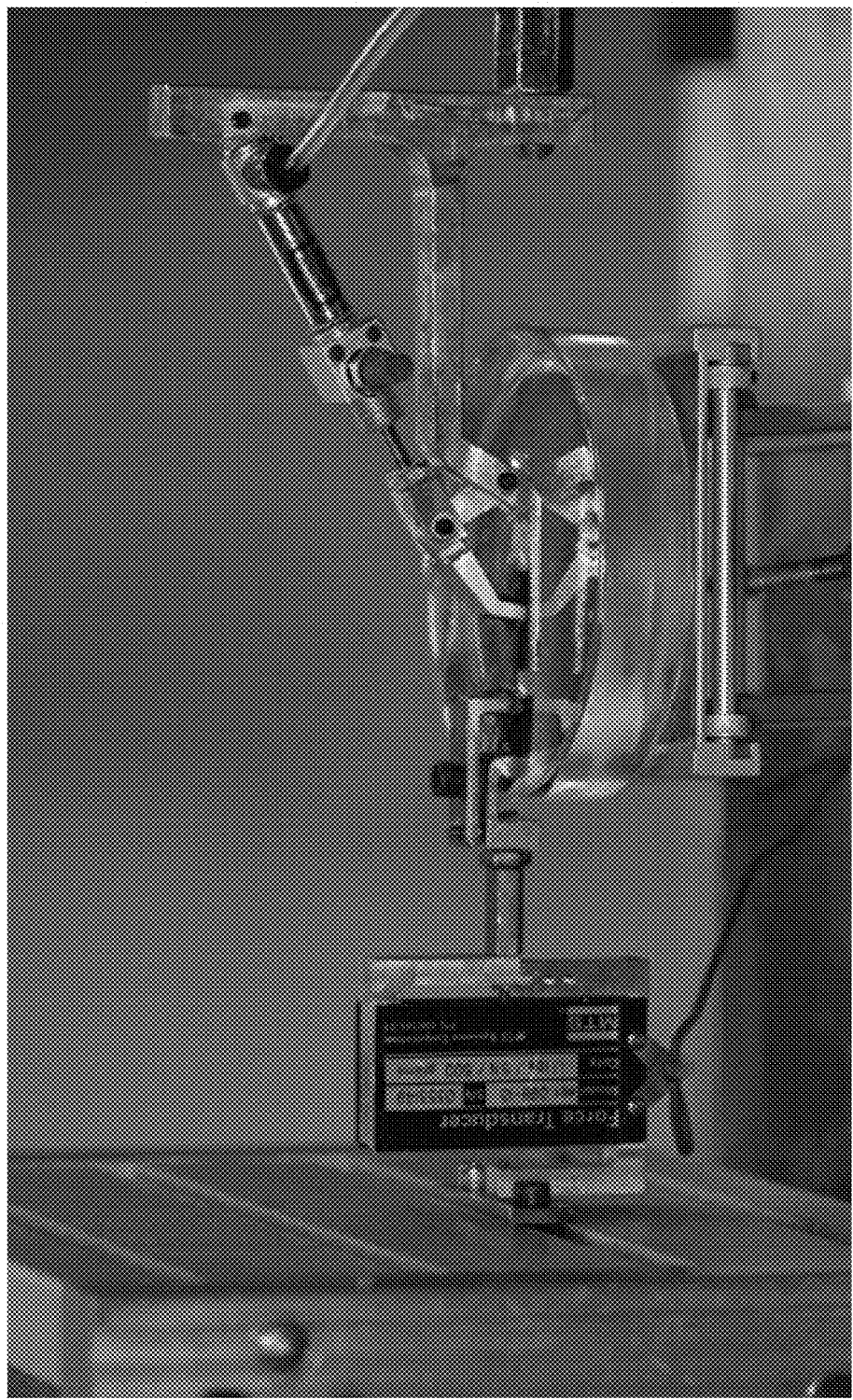
FIG. 2 is an illustration of a testing apparatus for conducting uniaxial testing to determine viscoelastic mechanical properties of specimens.

FIG. 1 shows a flow diagram of an example method for forming a representative tissue model. In an example, a method of making or developing a tissue model can include determining one or more material properties of a tissue, such as a mammalian tissue, for example human tissue. The tissue can be a specific type of tissue upon which training is desired (e.g., fat, connective tissue, nerve, artery, vein, muscle, tendon, ligaments, renal artery tissue, kidney tissue, ureter tissue, bladder tissue, prostate tissue, urethra tissue, bleeding aorta tissue, pyeloplasty tissue, Y/V plasty tissue, airway tissue, tongue tissue, hand tissue, general skin tissue, specific face skin tissue, eye tissue, brain tissue, vaginal wall tissue, breast tissue, nasal tissue, cartilage, colon tissue, stomach tissue, liver tissue, rectal tissue, heart tissue, bowel tissue, pancreas tissue, gallbladder tissue, liver tissue, inferior vena cava tissue, aortic tissue, lung tissue, bronchial tissue, soft palate tissue, larynx tissue, pharynx tissue, epidermis tissue, dermis tissue, lip tissue, mucosal membrane tissue, or adhesion tissue, just to name a few). The material property of the tissue can include mechanical properties (such as viscoelastic properties, nanoindentive properties, strain rate insensitivity, compressibility, stress-strain curves, Young's modulus, yield stress, tear point, deformability, and the like), electroconductive properties, thermoconductive properties, optical properties, chemical properties, or anisotropic properties. Methods of testing tissue and determining specific material properties can be according to methods known in the art. For example, mechanical properties can be determined by the viscoelastic mechanical properties are determined by uniaxial, biaxial, nano-indentation, relaxation, creep, or shear testing of the native tissue. FIG. 2 shows an example of a uniaxial testing apparatus for determining viscoelastic mechanical properties of a tissue or a tissue model.

After determining the one or more material properties of the tissue, such as one or more constitutive properties of the tissue, the method can include creating an anatomical structure of the tissue, followed by coupling an artificial tissue material to the anatomical structure. The anatomical structure can include a base structure having a geometry that is representative of a corresponding anatomical structure, such as within a mammalian body. For example, if a model of the human hand is desired for training regarding treatment of a skin wound, than the anatomical structure that is formed can simulate the bones and underlying musculature, ligaments, and cartilage of the hand. The artificial tissue material can simulate one or more skin layers of the skin of the hand. The anatomical structure and the artificial tissue material can include more or less of the underlying structure, depending on how much of the tissue is desired to be simulated. For example, if only the skin need be simulated in order to allow a trainee experience with stitching of simple wounds, then the artificial tissue material can simulate only the skin tissue (e.g., the dermis and the epidermis). However, if it is desired to simulate a portion of the muscle tissue as well, such as to train on more advance tissue repair, the artificial tissue material can simulate at least a portion of muscle tissue as well.

In an example, the material of the tissue model can be selected or made to have material properties that substantially correspond to the corresponding material properties of the tissue being simulated. By "substantially correspond," as used herein, can refer to a particular material property being within 10% of the value of the same material property in the native tissue, such as within 9%, 8%, 7%, 6%, 5%, 4%, 3%, 2%, or 1%. In an example, each of the material properties being simulated is within about 2% to about 4% of the corresponding material property of the native tissue.

The material property or properties of the tissue model that substantially correspond to the same material property of the native tissue can depend on the purpose for the simulation. In most examples, the tissue model can be designed to simulate native tissue for a particular medical procedure where the tissue is to be physically manipulated by a user, such as a surgical procedure. In these examples, at least one or more mechanical properties of the tissue model substantially correspond to the same mechanical property in the native tissue being simulated. For example, the tissue model might have a viscoelasticity, a compressibility, and a tear stress that substantially corresponds to a viscoelasticity, a compressibility, and a tear stress of the native tissue or tissues. Additional mechanical properties may be included to substantially correspond to those of the native tissue so that the tissue model will feel and behave substantially the same as the native tissue, particularly in the view of an expert in the procedure being simulated.

Other types of material properties can be included, in addition to mechanical properties, to increase the fidelity of the tissue model for the procedure being simulated. If the procedure being simulated includes cauterizing or some other thermal manipulation of the native tissue, then the tissue model can also include one or more thermoconductive properties that substantially correspond to thermoconductive properties of the native tissue. Similarly, if the procedure being simulated includes the use of optical inspection, such as imaging of the native tissue, then one or more optical properties, such as reflectivity, light transmission of a particular wavelength or range of wavelengths, or light absorption of a particular wavelength of range of wavelengths, can substantially correspond to the same one or more optical properties of the native tissue. Similar considerations can be made for electroconductive properties, nano-indentive properties, chemical properties, or anisotropic properties (e.g., the value of a particular property, including mechanical, electrical, thermal, optical, or chemical, in one direction versus another direction).

In some examples, two or more of the material properties, such as three or more, four or more, five or more, six or more, seven or more, and so on, of the material properties listed above, substantially correspond to the corresponding material properties of the native tissue.

The physical properties that can be considered for soft tissues include homogeneity, nonlinear large deformation, anisotropy, viscoelasticity, strain rate insensitivity and compressibility. A human tissue database can include tissue characteristics data that provide values for comparison with simulator materials.

The creation of a human tissue property database can provide for accurate constitutive computer simulation models of structures, injury and disease. The primary components affecting the creation of artificial tissue models are material costs and supplies, accurate anatomical modeling, knowledge of the mechanical properties of the represented tissues, choosing the right materials, assemblage of the models in an accurate representation of human anatomy, and model development based on educational principals and "backwards-design" with an embedded-assessment strategy to maximize the learning.

In an example, data regarding material properties of tissue to be simulated is determined by harvesting soft-tissue specimens within 24 hours of death of a subject. The specimens are warmed to body temperature and then subjected to uniaxial or biaxial testing to determine viscoelastic mechanical properties. In addition, electroconductive, thermoconductive, and indentation experiments can be performed on a plurality of different tissue types. The data is then stratified according to gender, age, and body mass index (BMI).

In an example, data from the testing of the tissue samples is used to form a tissue database, such as a human tissue database, which can be used to guide the formulation of organo silicate base material with the objective of tailoring the recipes of artificial tissues to match the properties of fresh human tissue.

In an example, analyzing the similarities between human tissue materials and simulation materials is to compare characteristics of their stress-strain curves. The stress-strain curves can be generated by a preprogrammed routine in Excel on an MTS computer based on inputted width, thickness, and initial displacement values and load vs. extension data. Engineering stress is defined as a force per unit area:

$$\sigma = \frac{F}{A} \quad [1]$$

where F is the applied force and A is the cross sectional area. Green strain is defined as:

$$G = \frac{1}{2}\frac{(L_o - L^2)}{L^2} \quad [2]$$

where $L_0$ is the original length of the sample and L is the final length of the sample. The Young's modulus can be found by taking the slope of the stress-strain curve at the initial linear portion modulus of the graph. Yield stress is defined as the stress at which the material begins to break and can be found on the stress-strain curve as the maximum stress value on the stress-strain curve. The corresponding strain value is defined as the strain at yield.

The data from the human tissue database allows tailoring of the organosilicate base material. Simulator models can be produced using commercially available off-the-shelf (COTS) organosilicate materials. The base material can undergo modifications to change cross-linking, electrical conductivity, thermal conductivity, reflectivity, indentation, odor, and color. Pigments and dyes can be added to the organosilicate material to create anatomically accurate color mapping of the simulator model.

The materials used to create human tissue analogues need to meet many specifications in order to successfully emulate actual human tissues. In some examples, organosilicate materials are used as the base material for creating artificial tissues. Commercial off the shelf (COTS) organosilicate materials can undergo repeated cycles of revision by continually comparing testing data of the artificial tissue to the human tissue database.

Organosilicate materials are stable and do not require specialized storage or shipping. These materials are cost effective and are less expensive as compared to animal and cadaveric models. The material is durable and can often be reused which also adds to cost-effectiveness.

The organosilicate polymer base material is mostly clear in color and is capable of being cured in room air or within a mold. The polymer base material is mixed thoroughly with additives, resins, or indicators to allow for equal distribution of the base throughout the combined mixture. The mixture is placed in a mold to form a molded sample layer by layer. Once fully cured, the mold is de-cast, and the molded sample is coated with a talcum powder and is washed with cold water to remove excess talcum powder.

Reflectivity is a factor in ultrasound and fluoroscopy procedures. The organosilicate materials of the tissue models of the present disclosure have demonstrated useful reflectivity properties with respect to ultrasound and fluoroscopy. This reflectivity allows the materials to be used in simulated procedures such as ultrasound and fluoroscopy.

Possible modifications affecting viscoelastic properties include ratio changes, chemical additives and ultraviolet (UV) light exposure. For example, organosilicate films that are exposed to an ultraviolet light source have at least a 10% or greater improvement in their mechanical properties (i.e., material hardness and elastic modulus) compared to the as-deposited film (U.S. Pat. No. 7,468,290). The UV light has been shown to cause increased cross-linking in the material, which can increase the modulus and decrease the elasticity (Crowe-Willoughby et al., 2009). In some examples, the intensity and duration of UV exposure can be modulated to provide for fine-tuning of desired mechanical properties.

In an example, silicone-based materials are useful in simulation and biomedical applications. Silicon is an element that is rarely found in its elemental form but can be found as oxides or as silicates. Silica is an oxide with formula $SiO_2$ that can have amorphous or crystalline structure. Silicates are salts or esters of silicic acid (general formula $(SiO_x(OH)_{4-2x})_n$) that contain silicon, oxygen, and metal elements. Silicones are polymers made of silicon, oxygen, carbon, and hydrogen with repeating Si—O backbone (Colas, 2005). These polymers are created synthetically with the addition of organic groups to the backbone via silicon-carbon bonds. A common silicone is polydimethylsiloxane (PDMS) with monomeric repeat unit (e.g., $SiO(CH_3)_2$). The number of repeat units and degree of cross-linking within the silicone polymer can account for the different types of silicone materials available for different applications. Silicones have been used in biomedical applications because of their high biocompatibility, their chemical inertness, and their resistance to oxidation.

In an example, the material of the tissue model can comprise platinum based silicone-rubbers, tin cured silicone rubbers or urethane rubbers. The sources and trade names of these materials are presented in Table 1. Table 2 provides the foams and additives used in the present application.

In an example, the organosilicate base can be a soft, room temperature vulcanized (RTV) silicone rubber with a hardness of less than 30 shores. The two-part component can be addition cured and platinum catalyzed to result in high tear strength and flexible mold compounds. The organosilicate base can bond to plastics. The percentage of mixing of A and B change depending on the application of the tissue model.

In an example, a platinum salt in portion B (OSHA PEL and ACGIH threshold limit value 0.002 mg/m$^3$ (as Pt)) has the following technical specifications.

| | | |
|---|---|---|
| a. | Mix ratio, by weight | 1A:1B |
| b. | Hardness, Shore A | 10 ± 2 |
| c. | Pour time, minimum | 6 min |
| d. | Demould time @ 25° C. (77° F.) | 30 min |
| e. | Color translucent/Colorless | off white |
| f. | Viscosity, mixed | 15,000 cP |
| g. | Specific volume (in$^3$/lb) | 25 |
| h. | Specific gravity @ 25° C. (77° F.) | 1.10 |
| i. | Shrinkage upon cure | Nil |
| j. | Flash point > 350° F. | |

In an example, a tissue-specific organosilicate base material is formed onto the three-dimensional model, such as by painted layering, casting, depositing, molding, printing and the like. The organosilicate base material conforms to the details of the model to create an exact replica of the patient specific anatomy.

In an example, organo silicate material is added in precise layers to imitate the physiologically distinct layers found in skin and other human tissues. In an example, a first layer of a first organosilicate material is applied to the three-dimensional printed model and allowed to cure to simulate a first layer of tissue. A second layer of a second organo silicate material is applied to the first layer, wherein the second organo silicate material can be different than or the same as the first organo silicate material and allowed to cure to simulate a second layer of tissue. Subsequent layers (e.g., a third, fourth, and fifth layer, etc.) can be added over the second layer. The layers might not all be cured in between if the layers are to be inseparable. However, substances, devices, sensors can be added between or within each layer.

In an example, one thick layer of a first organo silicate material or a plurality of thin layers of the first organosilicate material can be applied to the three-dimensional model in order to simulate a substantially uniform tissue structure or layer. Once the material layer or layers have been added to the desired thickness, the outer material can be separated from the mold and sealed.

Figures 6A, 6B, 6C:
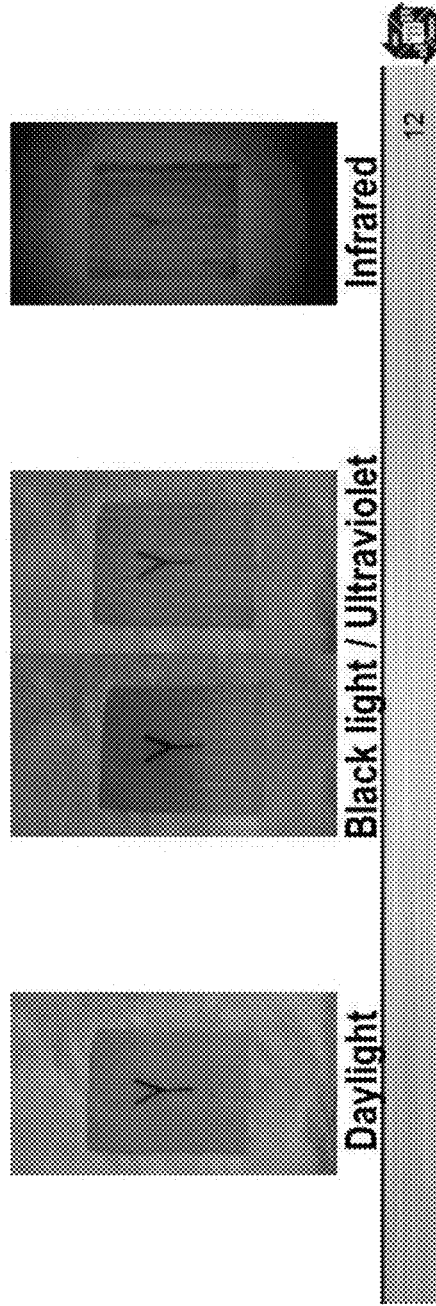
FIG. 6A is an illustration of black light assessment of surgical techniques (BLAST) skin Model with rare earth element based coating under normal light.
FIG. 6B is an illustration of BLAST skin model with rare earth element coating under UV black light.
FIG. 6C is an illustration of BLAST skin model with rare earth element coating under IR light.
Figures 9A, 9B, 9C, 9D:
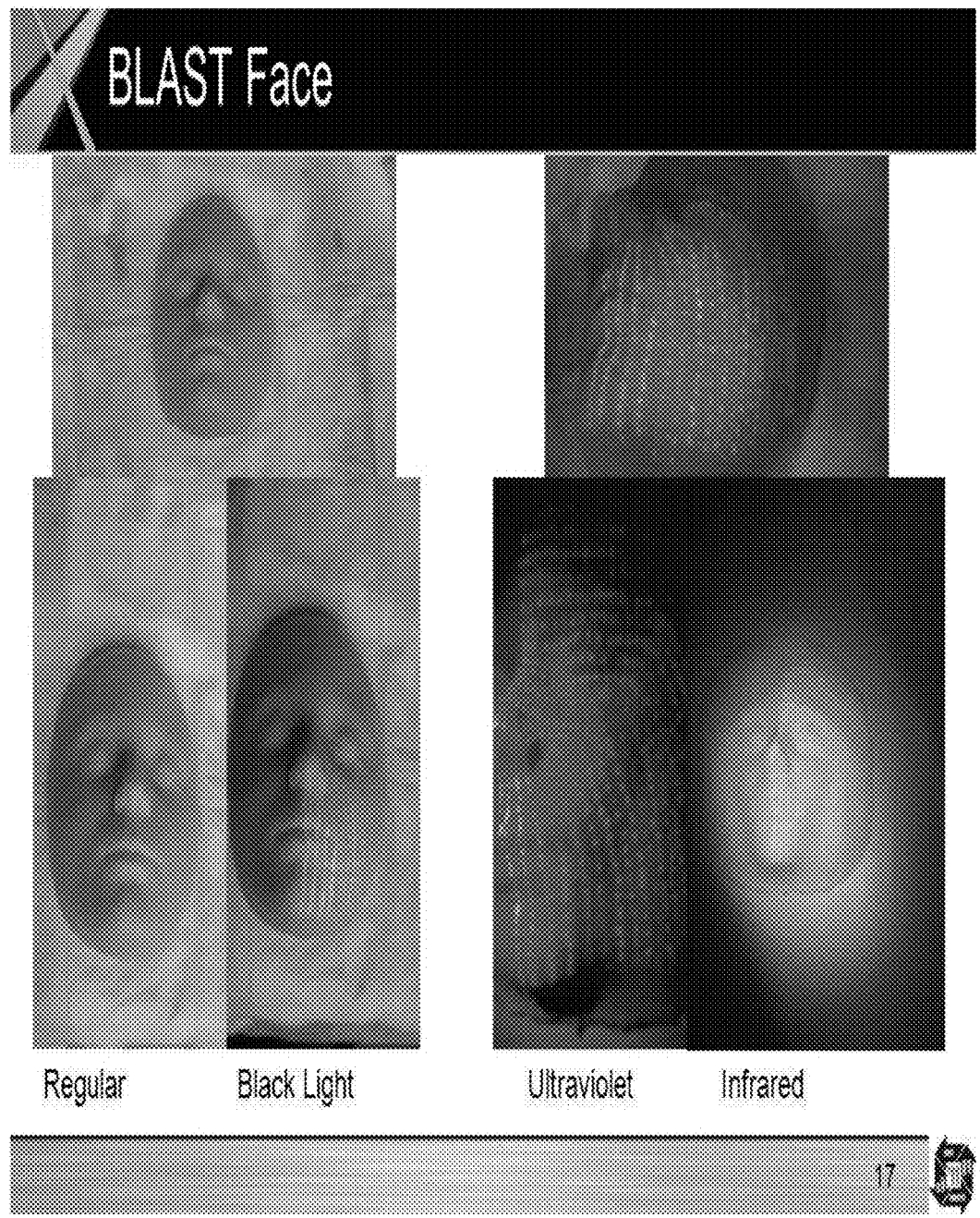
FIG. 9A is an illustration of BLAST face Model with rare earth element based coating under normal light.
FIG. 9B is an illustration of BLAST face model with rare earth element coating under black light.
FIG. 9C is an illustration of BLAST face model with rare earth element coating under UV light.
FIG. 9D is an illustration of BLAST face model with rare earth element coating under IR light.

The simulator materials can also be implemented with indicators that can provide for evaluation of the proficiency of a trainee to perform certain skills. Synthetic, photochromic, thermochromic, solvatochromic, or piezochromic materials can allow for color change based on light that the material is exposed to, heat that the material is exposed to, chemicals that the material is exposed to, or pressure applied to the material. FIGS. 6A to 6C successfully demonstrate black light assessment of surgical technology (also referred to as "BLAST") for embedding performance assessment in a model. Similarly, FIG. 9D demonstrates infrared light assessment of surgical technology (IRAST) for embedding performance in a model. In this case, lines invisible to the user (FIG. 6A) can be assessed after a tissue approximation exercise allowing his or her ability to perform a desired task. In an example, photochromatic materials that change color based on contact or pressure can provide a non UV-based goal for measurement. A thermochromatic material exposed to heat can also be used, and would produce a similar effect. Chemical indicators can also be used using a steam, or chemical acid/base interaction and can provide similar results.

In an example, an indicator material can be added within or in between one or more layers of the organosilicate tissue model in order to provide for skill proficiency training and evaluation. The indicator material can be added as lines, dots, or other indicating patters that can be used to indicate or determine proper performance of a particular task. In an example, the indicator material can be applied on an outer surface of the tissue model with a predetermined pattern that can be compared to an ideal pattern for a particular procedure. In another example, the indicator material can be embedded within the tissue model material so that the indicator material is only exposed if and when it is exposed by cutting or removing a portion of the artificial tissue model. The indicator material can be configured to be exposed when a procedure is performed correctly, e.g., when an incision or dissection is performed properly, or the indicator material can be configured to be exposed when a procedure is performed incorrectly, e.g., when a portion of the tissue model is incorrectly removed or exposed, or both.

Figure 13:
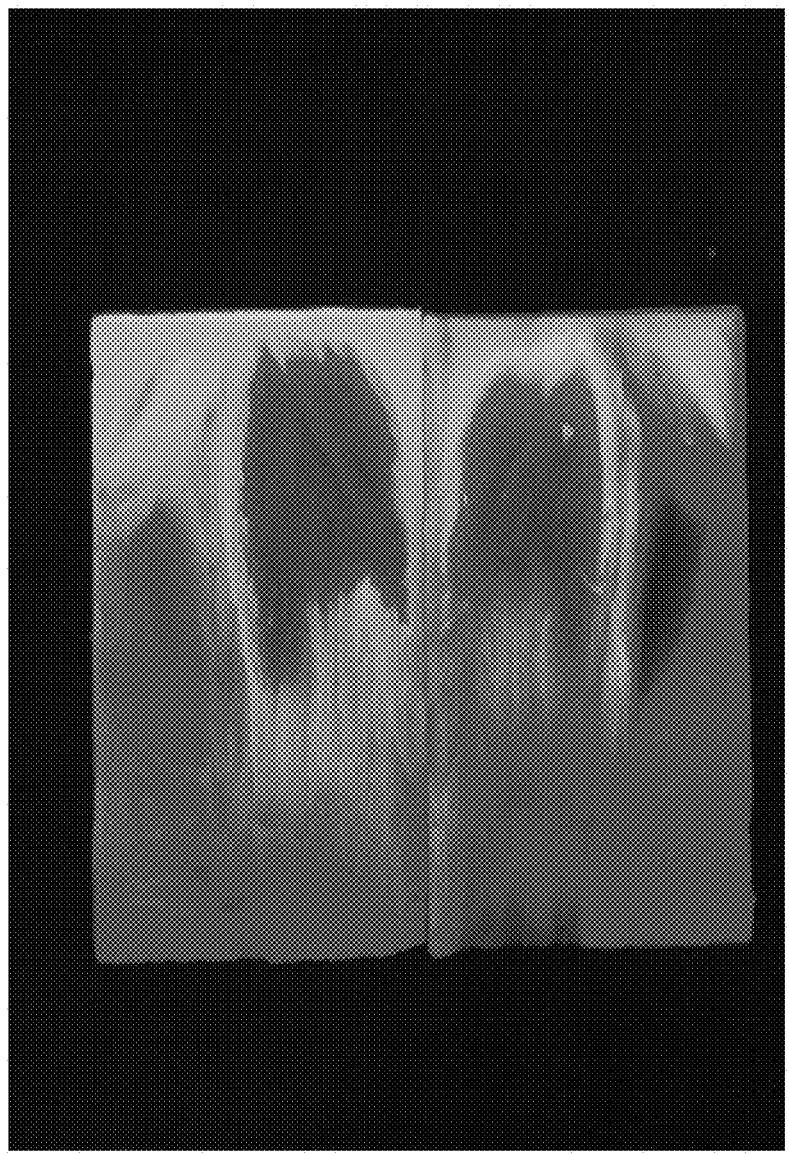
FIGS. 13A-13B are illustrations of indicator material in between tissue layers.
Figure 13:
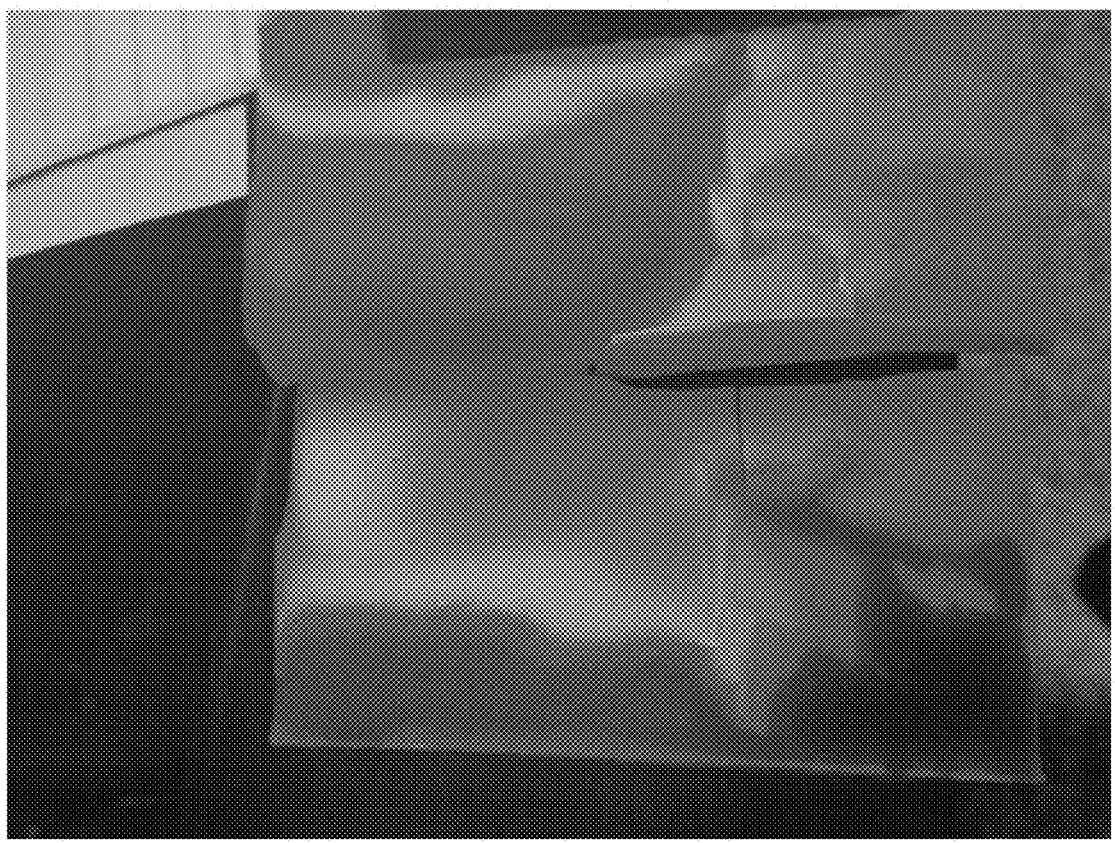

In an example, the indicator material can be visible to a user, e.g., a trainee, to indicate the proper position for a particular portion of a procedure, e.g., the location where a trainee should perform a particular action, such as clipping, cutting, or suturing the tissue model. The amount of indicator used can depend on an application, depth that the indicator layer is placed, and the color of substrates and layers as shown in FIGS. 13A and 13 B.

In an example, the indicator material is selected to be undetectable by a user of the tissue model, such as a trainee using the tissue model. In an example, the indicator material can be undetectable by being transparent or substantially transparent, so that the trainee will be unaware of the location of the indicator material. The indicator material can then be made to be visible to the trainee or an evaluator after completion of the procedure to determine the effectiveness of the procedure. The indicator material can also be used as a real-time indicator.

In an example, the indicator material can comprise an ultraviolet light or infrared light sensitive coating that can be added onto or into the simulated tissue, for example on one organo silicate layer or between the organo silicate tissue layers, at predetermined locations.

In an example, a polymer resin coating is applied to one or more organo silicate layers of the simulator model in lines, dots, or other patterns. While performing a specified task, such as a surgical procedure, the user (e.g., a trainee) is unaware of the polymer resin based coating patterns on the simulator due to the transparent nature under normal light (See FIG. 6A). Following completion of a task by the user, an evaluation of his or her ability to perform the task can be made by viewing the tissue model under UV light where the UV-sensitive coating pattern will appear (FIG. 6B).

In an example, UV-sensitive coatings can be applied to fluoresce in more than one color when exposed to UV light, such as a first color for a first pattern of UV-sensitive indicator coating, and a second color for a second pattern of UV-sensitive indicator coating. Indicator coatings can be especially useful in skill assessment involving matching or aligning tissues, such as for suturing or grafting.

A polymer resin can be created from UV pigments that are natural or synthetic minerals, and added to one part of the organo silicate base. The base is then agitated to ensure a complete homogenous mixture.

The pigments can be in powder form. Examples of pigments which make up the colors of blue, red, white, yellow, orange, or green may be selected from the following list of minerals: adamite, agate, albite, alunite, amber, amblygonite, analcime andersonite, anglesite, anthrophyllite, apatite, aphthitalite, apopyllite, aragonite, autunite, axinite, barite, becquerelite, boltwoodite, brucite, cahnite, calcite, caloimel, celestite, cerrusite, chondrodite, clinohedrite, corundrum, cowlesite, datolite, dioside, dypinite, espertite, eucryptite, fluorite, foshagite, gaylusite, gowerite, gypsum, halite, hanksite, hemimorphite, hydroboracite, idrialite, laumontite, magnesite, margarosanite, melanophlogite, mesolite, meta-autunite, meyerofferite, montebrasite, nahcolite, natrolite, norbergite, opal, pectolite, phosphuranylite, pirssonite, plombierite, powelite, pyrophylite, quartz, scapolite, scheelinte, smithsonite, sodalite, soddylite, sphalerite, spodumene, stilbite, strontianite, talc, thaumasite, thomsonite, tirodite, tremolite, trona, ulexite, uralolite, urannopilite, uranocirite, walstromite, wavellite, whewellite, willemite, witherite, wollastonite, wulfenite, wurtziste, xonotlite, zincite, zippeite, zircon.

Fluorescent pigments may be combined to create custom colors, that can match the tissue, or contrast based on need. Embedment of COTS indicators can also be used. An example would be of Clear Neon Black Light Paint.

In an example, the simulator models are produced by hand. The process for including the indicator material, such as a UV-sensitive material, on a tissue layer, in a tissue layer, or between tissue layers can be by hand painting or by spraying. Each type of rare earth element powder can be mixed separately or within some parts or with any of the additives such as thinners or thixotropic agents.

In an example, the ultraviolet light used to activate a UV-sensitive indicator material comprises UV A light having a wavelength of from about 340 nanometers to about 380 nanometers, such as about 365 nm. In some examples, the coating cannot be used in direct sunlight.

In an example, long wave fluorescent minerals, powders, or chemicals can be used to achieve a desired color, although short wave fluorescence or phosphorescence can show different colors.

In an example, household products such as cornstarch, tonic water (quinine), vitamin $B_{12}$, Woolight, Triethylamine, water based paints or fabric dyes can also be used. Some examples of colors and compositions of fabric dyes include, but are not limited to, white (agate, magnesium carbonate, or hydrated sodium calcium aluminum silicate); red (calcite, barium sulfate, halite, zinc iron sulfide, calcium fluoride, or quartz); orange (calcium fluoride, or zircon); yellow (calcium fluoride, or powellite); blue (calcium fluoride, fluorite, or calcite); green (calcium fluoride, zinc silicates, adamite, quartz, agate, or willemite); or purple (apatite or kunzite).

In an example, luminescent minerals such as petrolatum in fluorite can be used. In an example, phosphorescent minerals or chemicals can also be used.

In an example, the indicator material can be sprayed, hand painted, printed, silkscreened, or drawn in patterns that can be used for measurement or evaluation of performance, such as in a curricular or educational setting.

In an example, Smooth-On thinners are used and such thinners are applicable to all platinum cured silicones. The thinner can be composed of 100% dimethylsiloxane (CAS number 63148-62-9). Adding the thinner to the organosilicates can decrease the viscosity and durometer of the final material. The ultimate tear strength and tensile stress can also be reduced in proportion to the amount of thinner added. In an example, the maximum amount of thinner that can be added to a recipe is 15% of the weight of part A.

Additives can be added to reduce tackiness, decrease cross linking of the polymers (which makes them more fragile), increase lubricity (for a more viscous "feeling"), or increase the electrical conductive nature of the materials. In an example, the additives can include a silicone oil such as Dow Corning 200(R) fluid, 1CST (01013092) or octamethlytrisiloxanes (>60%). In an example, the additives can be at least one of petroleum jelly, glycerin, baby oil, talcum powder, colors, tints, dyes, metal wires, metal powders, nanotubules, theromochromatic pigments, slurries, water, and ink. Further, the additives can also be at least one of germanium wires, copper powders, nickel powders, dielectric inks, and dielectric coatings.

In an example, one or more sensors can be positioned on or between a layer or layers of the organo silicate tissue model or imbedded within one or more layers of the tissue model for measuring deformation of the tissue model, or force or pressure exerted on the tissue model, such as due to contact or collision with objects such as surgical instruments, hands of a medical practitioner, or other organs such as bones. In an example, the one or more sensors can be configured to perform an operation when a predetermined deformation, force, or pressure is sensed. For example, the sensor can be configured to record if and when a deformation, force, or pressure is exerted on the tissue model that corresponds to damage to the native tissue that the tissue model material is simulating. For example, if a particular native tissue is known to result in inflammation upon the exertion of a particular deformation, force, or pressure on the native tissue, than the sensor can be configured to record instances when that deformation, force, or pressure is reached. The sensor can also be configured to trigger an alarm or other notification that the predetermined deformation, force, or pressure had been experienced by the tissue model.

In an example, a piezoelectric film that can detect pressure or deformation can be used, such as the pressure or force sensing films sold by Tekscan, Inc. (South Boston, Mass. USA).

In an example, at least one of a strain gauge, a capacitive diaphragm, an electromagnetic inductance diaphragm, an optical strain detection sensor, a potentiometer mechanism, a vibration sensor, an accelerometer, a dynamic switch element, and a piezoelectric sensor can be positioned on or between or imbedded within any layer of the tissue model. In an example, the sensor can produce a voltage signal in proportion to a compression force, or a tensile mechanical stress or strain. Piezoelectric sensors, such as a piezoelectric film or fabric can also be well suited for high fidelity tissues with audio in the high frequency (e.g., greater than about 1 kHz) and ultrasound frequency (e.g., up to 100

MHz) ranges, such as for ultrasound detection. Piezoelectric sensors can be in the form of cables, films, sheets, switches, and can be amplified in a laboratory setting.

In an example, a piezoresistive sensor can be used to measure deformation of the tissue model material at a particular location. In an example, a piezoresistive fabric can be imbedded on, within, or between layers of the tissue model to provide contact and deformation detection with minimal delay in response or recovery time (over 400 Hz). A small delay in response or recovery time allows for haptic data of the interactions to be collected and for a dynamic response to be performed.

In an example, EeonTex flexible fabric (also known as e-fabric), sold by Eeonyx Corporation (Pinole, Calif. USA) can be used as a piezoelectric sensor that can conform with three-dimensional surfaces can be used.

In an example, a sensor can be located at an expected collision site. For example, while intubating the airway of an artificial tissue analogue, one or more sensors can be placed in at least one of an artificial tongue, an artificial larynx, an artificial pharynx, artificial vocal cords, and an artificial bronchii because these locations are known as collision sites where damage has occurred by improper technical or procedural technique. In an example, a sensor or sensors can be located near an incision site for the tissue model in order to measure the depth, pressure, and forces (with direction) of any movement of the tissue.

In an example, flow sensors can be imbedded into the tissue in order to measure flow rate, for example of a simulated blood flowing through the tissue model.

In an example, leak testing pressure sensors can be used to send the decay of pressure in an closed loop artificial artery or vein due to an accidental or purposeful cut, incision, or needle stick of the wall of the model. Quantifying the amount of fluid loss can be associated with blood loss in a patient during procedures, which can be related to outcomes and safety metrics.

In an example, determining the physical shape that the tissue model will take comprises creating a patient specific three-dimensional physical model via life casting, computer tomography (CT scan), or magnetic resonance imaging (MRI) datasets. In an example, DICOM imaging stacks are processed through compositing software (e.g., After Effects®) to identify and isolate the specific anatomical structure. The refined stack data can be processed through image segmentation software (e.g., Mimics®) to create a coarse three-dimensional model of the selected anatomy. The coarse model can be brought into a three-dimensional development package (e.g., Maya®) and used as a reference so that a new, clean model can be built over the previous model. The model can be further refined to the desired level of detail. The process can be guided by a physician or a subject matter expert. The subject matter experts include but not limited to engineers, physicians, anatomists, physiologists or biochemists.

Figure 3:
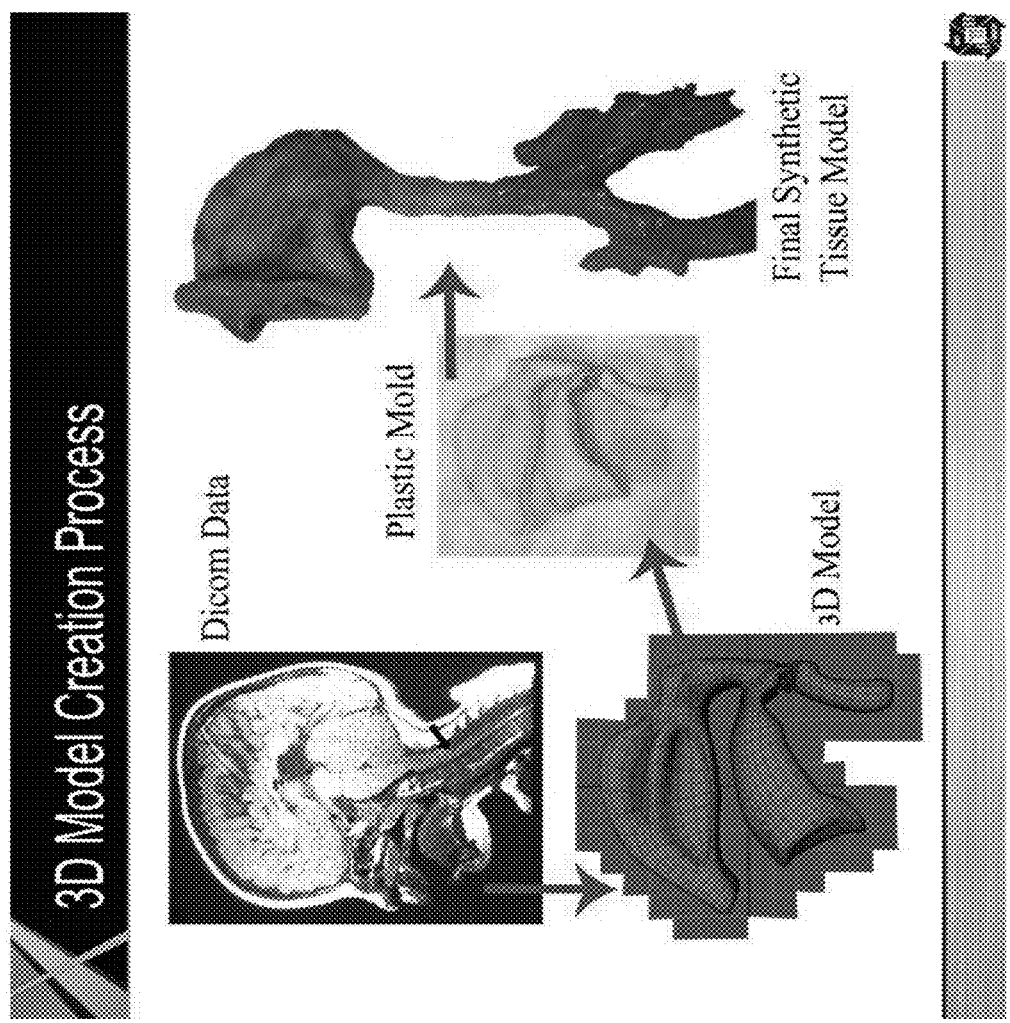
FIG. 3 is an illustration of overall process of creating a three-dimensional physical mold from patient specific data exemplifying pediatric airway.

In an example, forming the tissue model comprises sending the finalized virtual three-dimensional model to a three-dimensional printer that utilizes stereolithographic techniques to produce a three-dimensional printed model prototype or negative which is cast, created, or molded using the organosilicate base material determined from the tissue database. FIG. 3 shows an example process of forming a three-dimensional model of a patient's airway from an image take of the patient, such as an X-ray, CT scan, or MRI scan. The three-dimensional model can be used to form a mold. The base material, e.g., an organosilicate base material, can be applied to the mold, such as via painting, casting, molding, or printing, to form the final artificial tissue model.

The completed model can undergo face and content validation studies and testing by clinical and/or anatomy subject matter experts in the training environment to inspect any possible anatomical deviations. The anatomical deviations can include poor color mapping, visible seams or extra material pieces. Any abnormalities can be noted and corrections can be made to the protocol regarding the building of future models. As part of a curriculum, the models are assessed for their ability to provide face, construct, content, discriminate, concurrent, convergent, and predictive validity.

Figure 4:
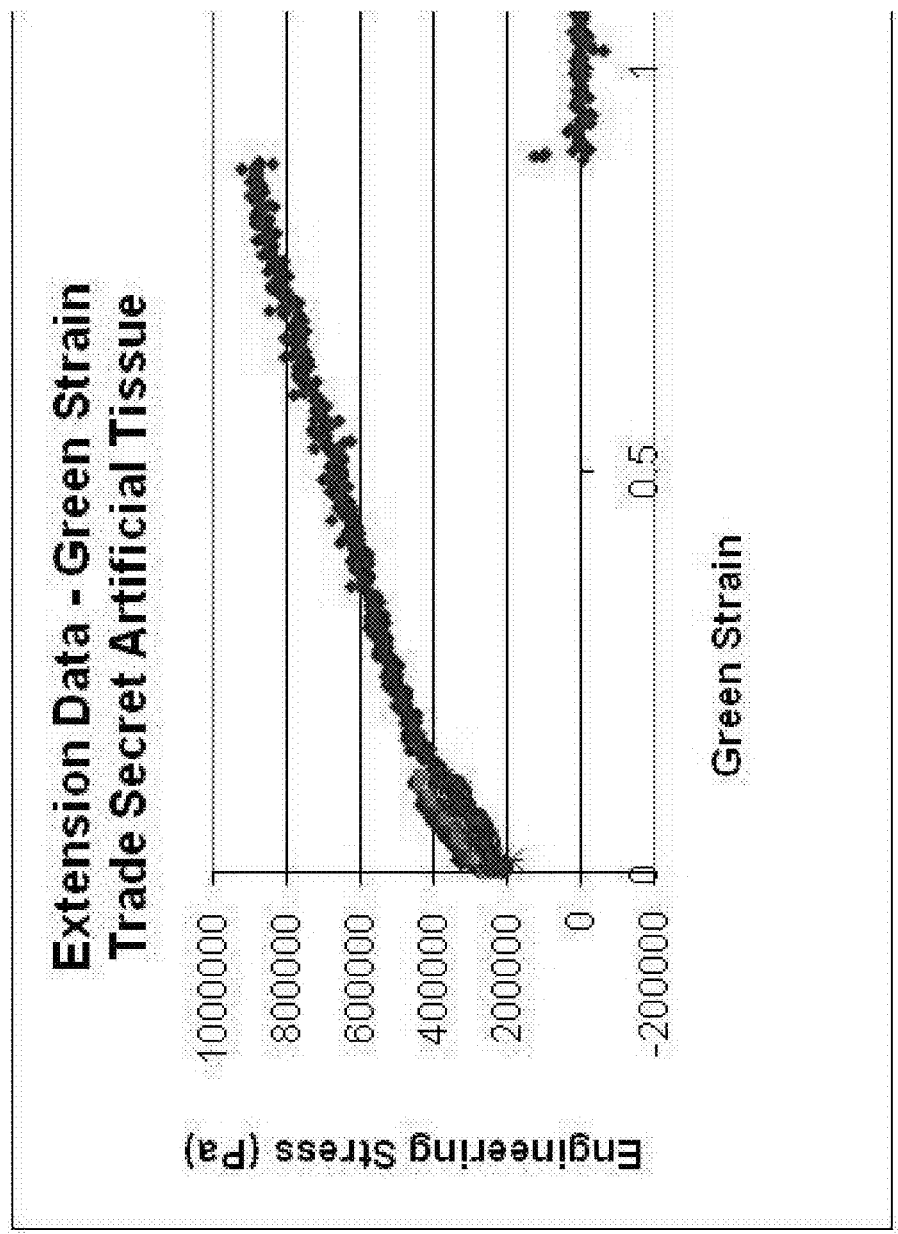
FIG. 4 is a graph illustrating stress-strain relationship for an artificial tissue.
Figure 5:
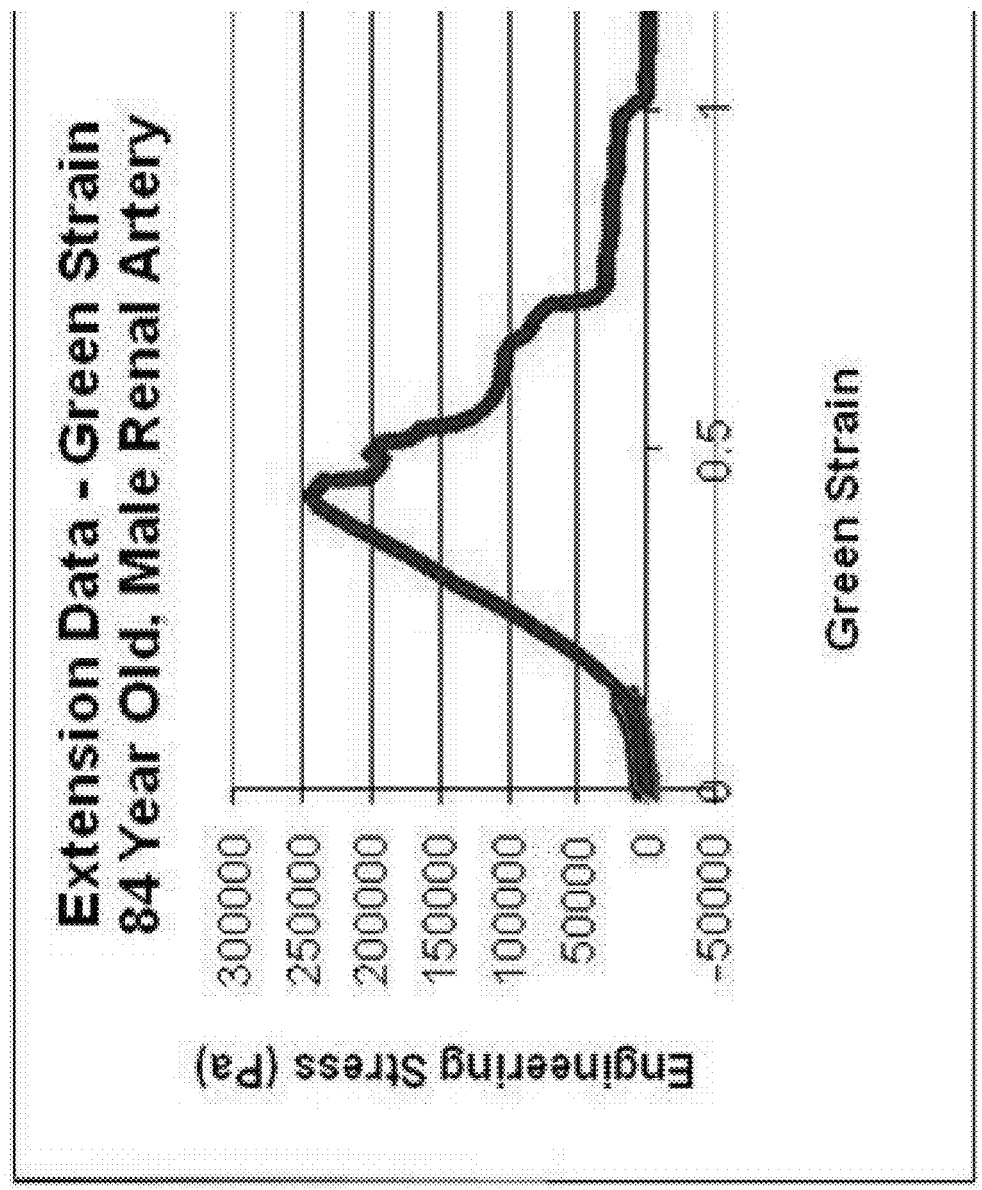
FIG. 5 is a graph illustrating stress-strain relationship for human renal artery.

Comparisons between the stress-strain relationships of the organosilicate based recipes and human renal artery have shown similarities in modulus, yield stress, and yield strain. FIG. 4 is an example of stress-strain graphs for an artificial renal artery tissue and FIG. 5 is an example of a stress-strain graph for actual human renal artery tissue. By comparing mechanical data obtained from these graphs, further improvement in human tissue to artificial tissue recipe matching can be made.

Stereolithography is advantageous due to the ability to rapidly create prototypes (typically less than one day). The resulting prototypes are durable and reusable as a positive or negative for tissue castings, adding to the cost-effectiveness of using stereolithography. The patient specific prototypes can also be made with as little as one datasets that are already collected for clinical purposes, expanding on the current use of medical technology and existing testing.

Prototypes created using stereolithography are anatomically accurate because of the detailed layer-by-layer process used to print the prototype. A stereolithography printer can be configured with high resolution that allows precise anatomical structures to be depicted in the printed prototype. A three-dimensional printed model can be made to be patient specific based on the original computer tomography (CT) or magnetic resonance imaging (MRI) images used. The models can also be used as a functional base for anatomical deviations and pathophysiology. One approach is to add a layer of wax over the three-dimensional printed model, which is sculpted to create bumps, detailing, or other deviations that can be desired for a specific training model.

The uses for physiologically accurate tissue simulators are widespread. Organosilicate based materials can be subjected to extremes such as cuts, burns, gun shots, and blast pressures. They can then be repaired by the trainee as part of a simulated procedure. They can also be repaired via exposure to UV lighting, reducing their cost, and increasing their usage.

The tissue simulators can be used independently or as hybrid models attached to standardized patients or confederates in training environments. The trainee is able to perform tasks such as needle sticks and suturing on the attached analogue tissues without harming the volunteer. The combination of patient interaction and accurate tissue simulation provides for an ideal training environment.

The completed tissue models can be used in combination with other substances in order to replicate a clinical situation. The organosilicate based tissue models can be used in the absence of silicone spray and can instead be implemented with inexpensive clinical substitutive artificial blood, saliva, urine, or vomit.

Examples of types of tissues that can be formed using the organo silicate base materials of the present disclosure include, but are not limited to: fat, connective tissues, nerve, artery, vein, muscle, tendon, ligaments, renal artery tissue, kidney tissue, ureter tissue, bladder tissue, prostate tissue, urethra tissue, bleeding aorta tissue, pyeloplasty tissue, Y/V plasty tissue, airway tissue, tongue tissue, complete hand tissue, general skin tissue, specific face skin tissue, eye tissue, brain tissue, vaginal wall, breast tissue, nasal tissue, cartilage, colon tissue, stomach tissue, liver tissue, rectum, and heart tissue.

Examples of types of tissues that can be formed using the organo silicate base materials of the present disclosure include, but are not limited to: bowel tissue, pancreas tissue, gallbladder tissue, liver tissue, Inferior Vena Cava, Aorta, Lung Tissue, bronchial tissue, soft palate tissue, larynx tissue, pharynx tissue, epidermis tissue, dermis tissue, lip tissue, mucosal membrane tissue, adhesion tissue. The present application benchmarked any inclusive tissues of the human tissue database.

Figure 10:
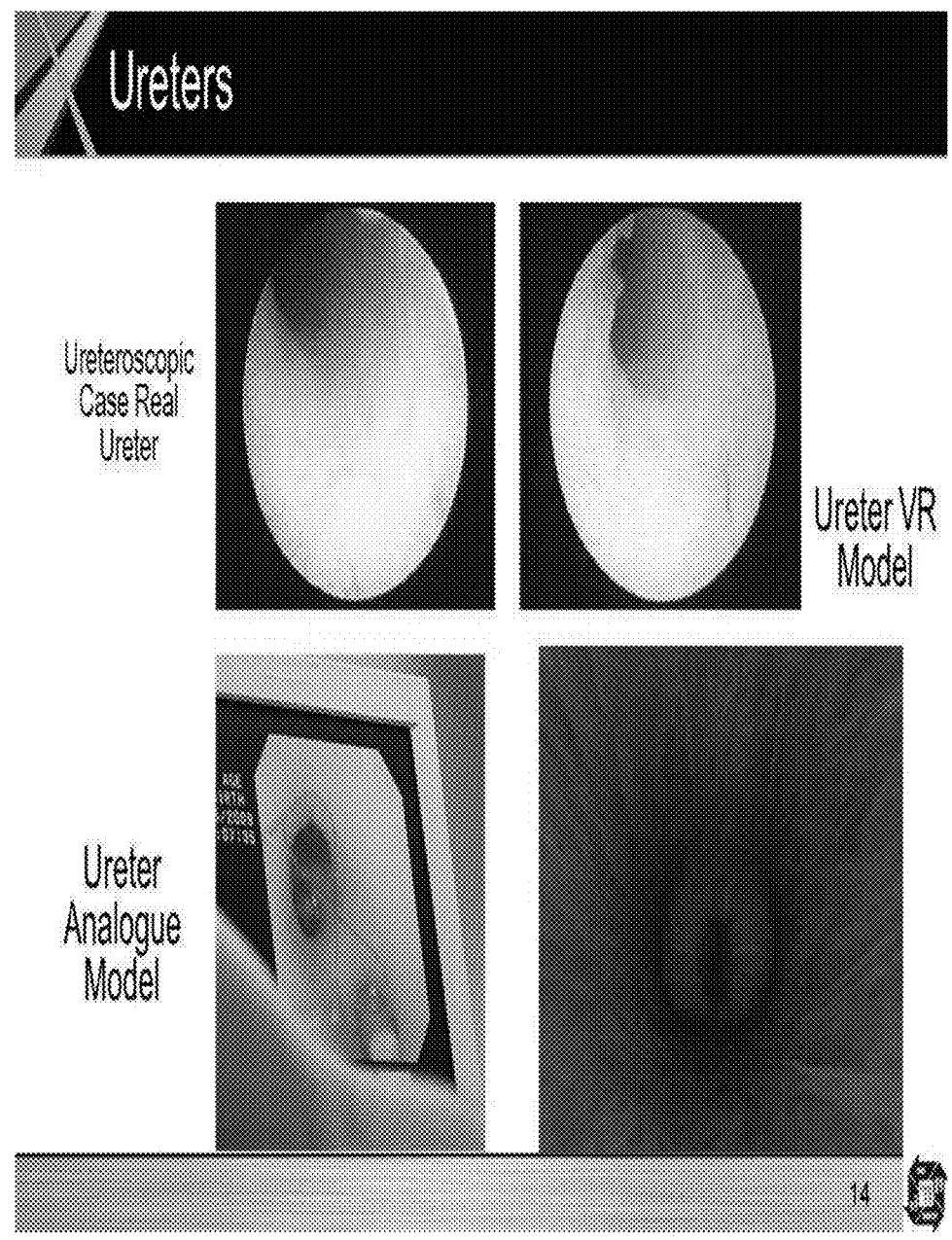
FIG. 10 is an illustration of animate ureter training model for endoscopy.
Figure 11:
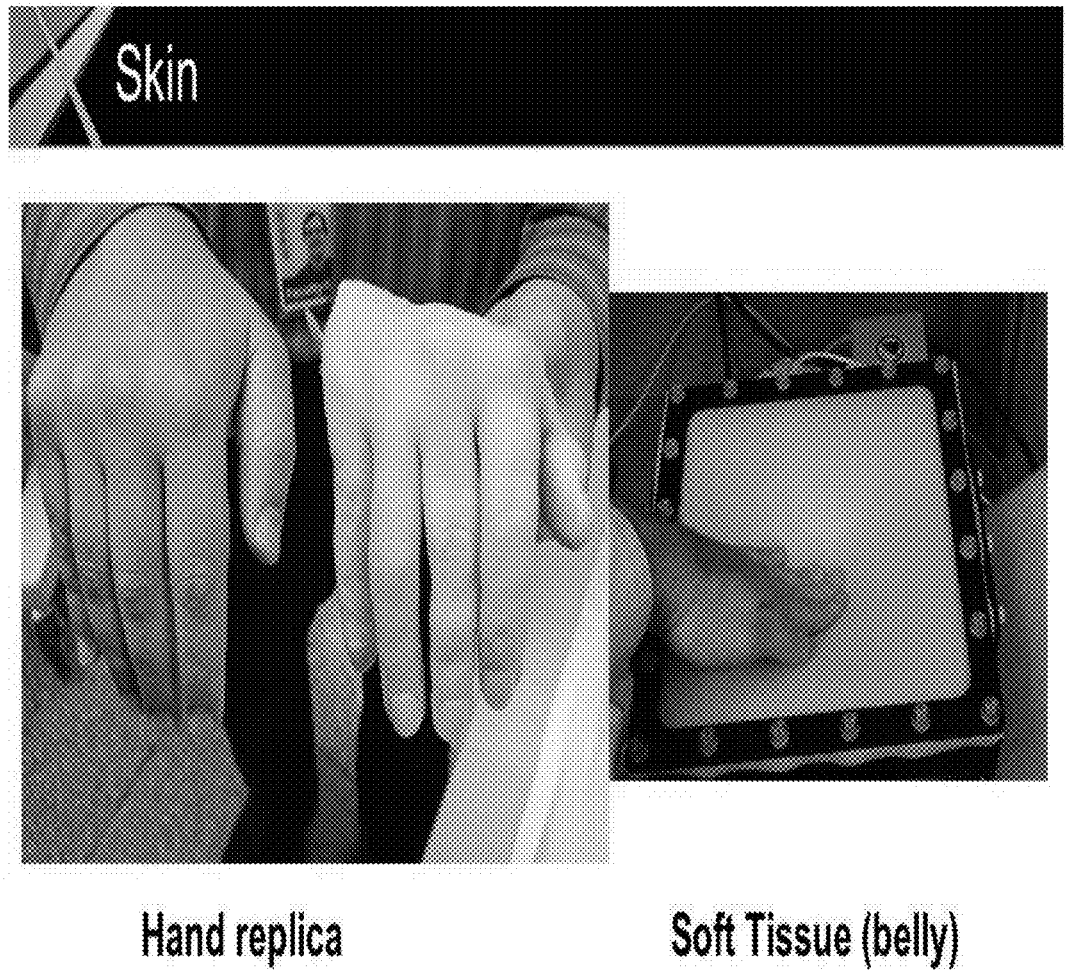
FIG. 11 is an illustration of animate hand training model for endoscopy.
Figure 12:
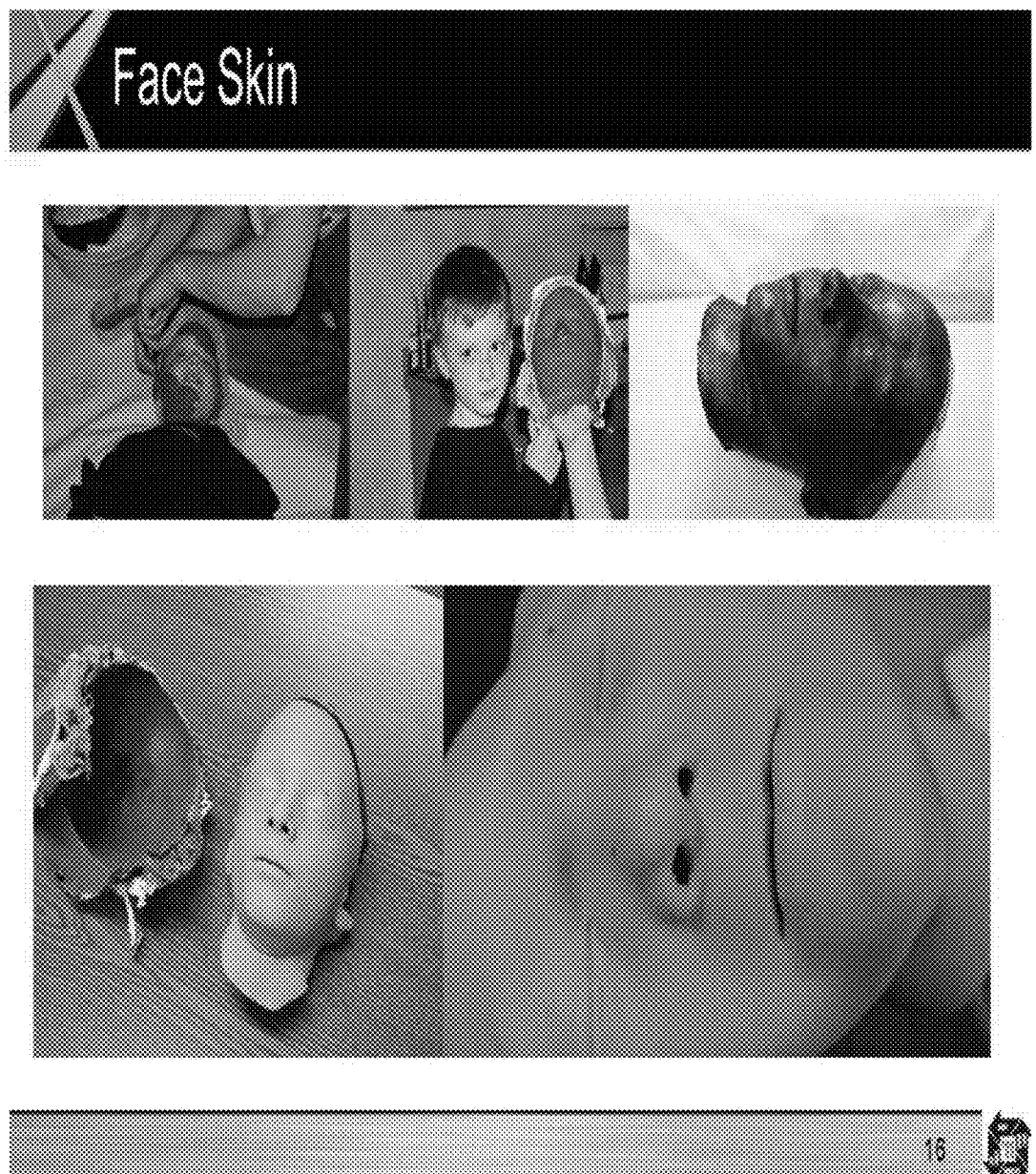
FIG. 12 is an illustration of animate face skin training model for endoscopy.

FIGS. 9-12 show examples of specific artificial tissue training models in accordance with the present disclosure. The artificial tissue training model has been created for a human face as shown in FIGS. 9A-9D. FIGS. 9A-9D also show an indicator material that has been placed on or within the artificial tissue that can be seen under various light sources, such as under an ultraviolet, or "black" light (FIGS. 9A, 9B, and 9C) or under an infrared light (FIG. 9D). FIG. 10 is an illustration of animate ureter training model for endoscopy. FIG. 11 is an illustration of animate hand training model for endoscopy. FIG. 12 is an illustration of animate face skin training model for endoscopy.

An entire segment of the body that has emulated physiology and accurate anatomical representation can be re-created relative to literature, data, studies, and testing. For example, for skin tissue, epidermis, demis, fat along with nerves, arteries, and veins, bones, muscle, and connective tissues can be created. The tissue models developed have the capability to define or create subtle differentiation of the stratum corneum, stratum lucidum, stratum granulo sum, stratum spinosum, and stratum basale.

EXAMPLES

Example 1 Renal Artery Simulator

Figure 7:
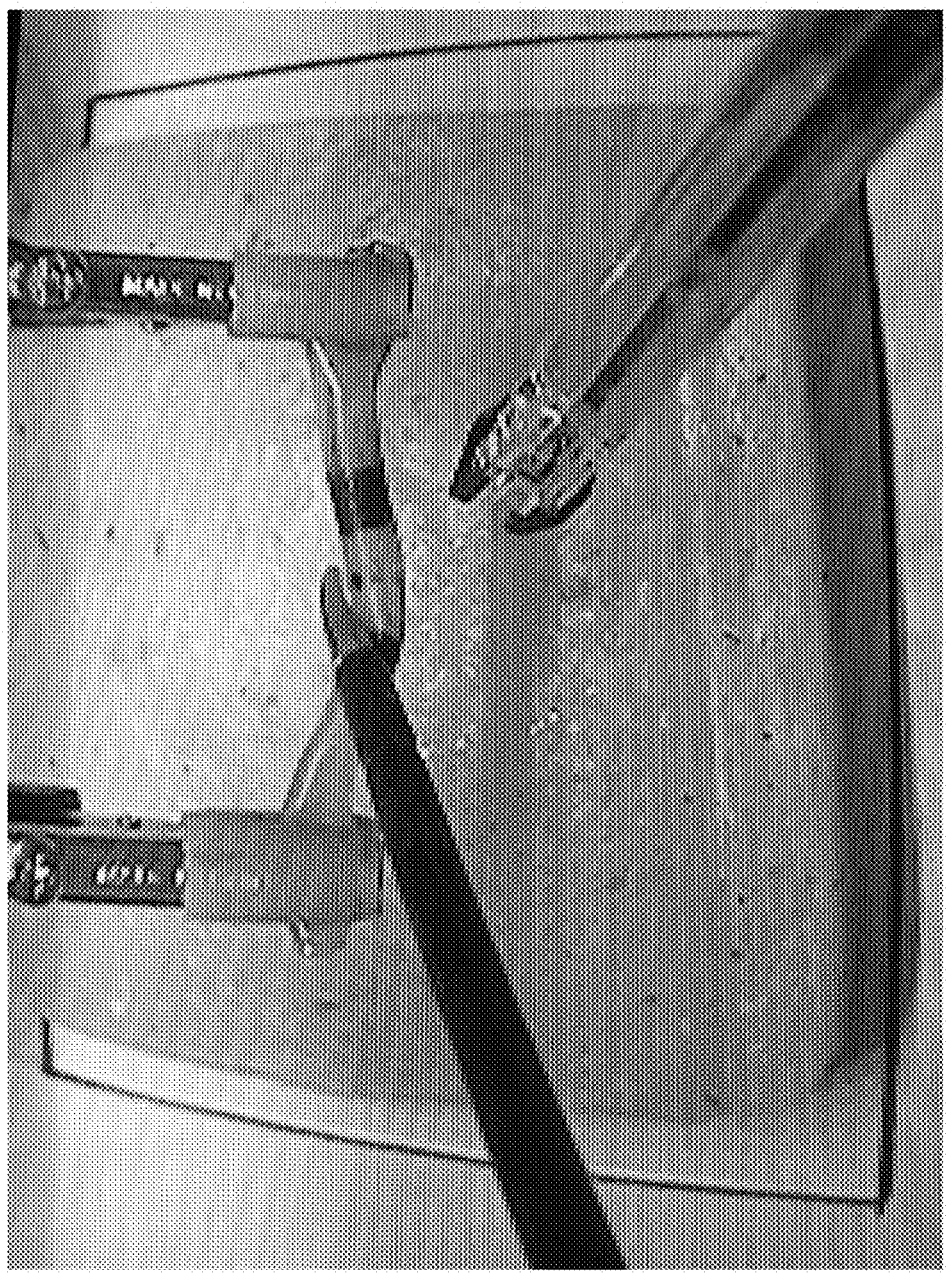
FIG. 7 is an illustration of animate renal artery training model with blood.

Using an organo silicate base material, the successful creation of an artificial tissue training model has been created for a human renal artery (FIG. 7) in order to meet the specifications of the American Urological Association for laparoscopic and robotic clip applying (Syverson, et al., 2011). The simulator tissue was color mapped to mimic human renal artery and filled with artificial blood to a mean arterial pressure (MAP) of 80±2 mmHG. Solid black pigment lines and dotted black pigment lines were added for training purposes to indicate areas for clipping and cutting respectively. The model was fitted into a mechanical apparatus to mimic a beating motion.

Example 2 Kidney Simulator

Figure 8:
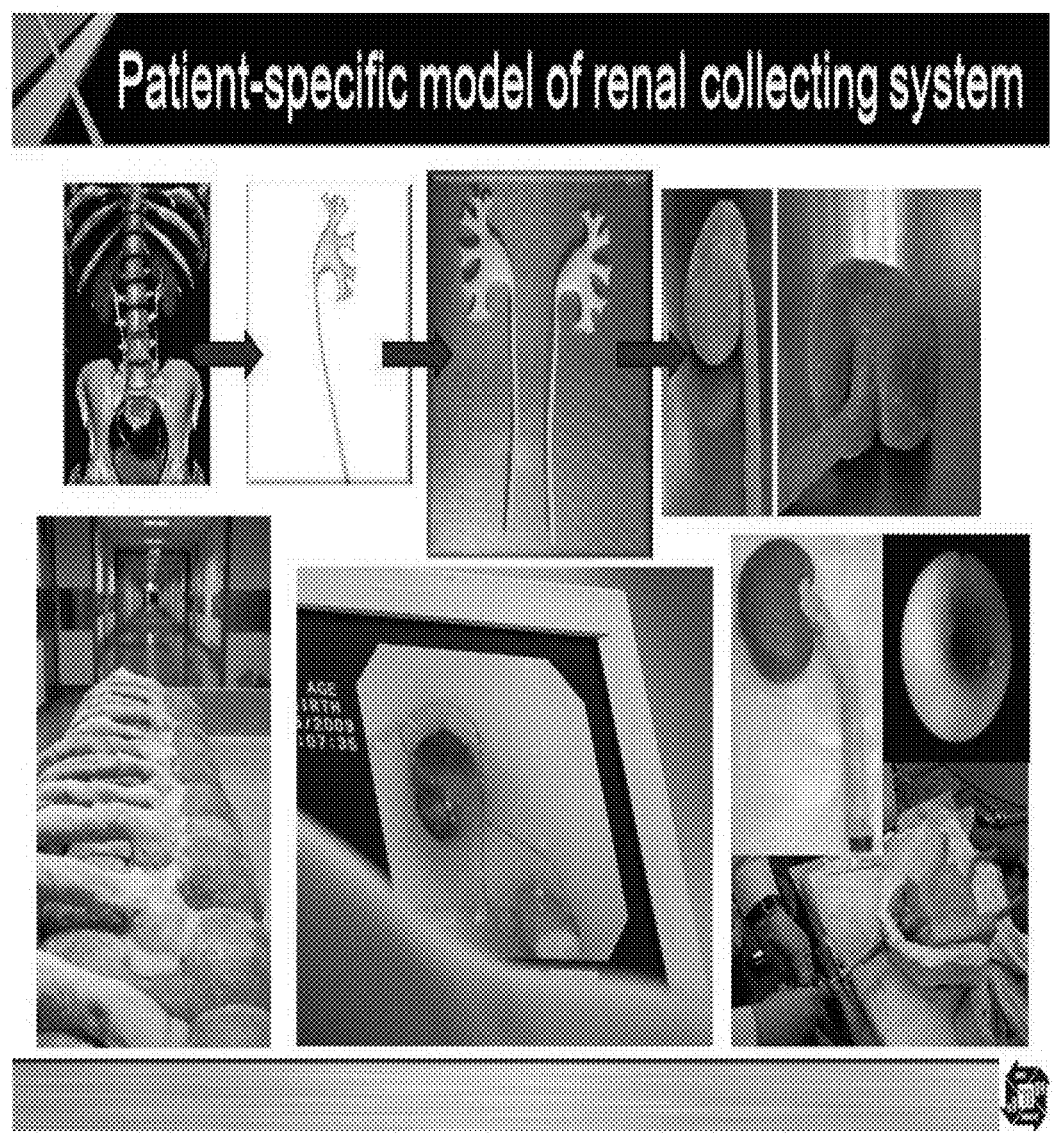
FIG. 8 is an illustration of animate kidney training model for endoscopy.

A kidney simulator (FIG. 8) was also developed using the techniques described above. The simulator utilizes renal tissue properties, e.g., from a human tissue database, accurate human anatomical modeling (stereolithographic prototyping) and color mapping to create realistic internal features such as the endoluminal ureter and the calyceal kidney collecting system. The model can be used in combination with artificial kidney stones and fluid to simulate procedures such as a ureteroscopy (FIG. 9), retrograde pyelography, ureteral stent placement, nephro-lithotomy, laser and extra-corporeal lithotripsy and kidney stone extraction.

In conclusion, the overall method for developing artificial tissue simulators for training purposes provides accurate anatomical modeling and matching of tissue properties. The materials and fabrication techniques are cost-effective and allow for the integration of indicators to properly evaluate trainee skill acquisition. The resulting tissue simulators can be applied to countless tissue types and training strategies to improve patient care through better procedural practice and assessment.

TABLE 1

Organosilicate base materials

| Type | Category | Company | Product Trade Name |
|---|---|---|---|
| Bases | Tin Cured Silicone Rubber | Smooth ON | Mold Max Series |
| | | Smooth on | Mold Max T-series |
| | | Smooth on | Mold Max STROKE |
| | | Smooth on | Mold Max XLS II |
| | | Smooth on | OOMOO Series |
| | | Polytek | TinSil 70 & 80 Series, |
| | | Dow Corning | Silastic Series |
| | | Silicones, Inc. | G1-650, 384, 1000, 1032, 1040, 1100, 1120, 1210, 1220, 184 |
| | | Silicones, Inc. | XT 153, 177, 314, 385, 386, 426, 464, 475, 479, 493, 585 |
| | Platinum Based Silicon Rubbers | Smooth on | Mold Star 15, 16, and 30 |
| | | Smooth on | Smooth-Sil |
| | | Smooth on | Dragon Skin Series (incl Fx Pro) |
| | | Smooth on | Ecoflex Series |
| | | Smooth on | Rebound 25 and 40 |
| | | Smooth on | Sorta Clear |
| | | Smooth on | Body Double |
| | | Smooth on | Skin Tite |
| | | Smooth on | Psycho Paint |
| | | Polytek | Platsil Series 71, 73, and Gels |
| | | Dow Corning | Silastic Series |
| | | Dow Corning | Xiameter Series |
| | | Silicones, Inc. | P series (incl. 656, FDA, 157, 125, 100, 90, 70, 60, 50, 45, 44, 20, 17, 15, 4, 10, 149, 163, 268, 288) |
| | | Silicones, Inc. | XP series (incl. 149, 163, 288, 344, 368, 378, 382, 429, 450, 536, 541, 549, 550, 573, 657) |
| | | NuSil | LSR elastomers (Med 4805, 4810, 4815, 4820, 4830, 4840, 4842, 4714, 4905, 4900 Series, 50/5800 series) |
| | | NuSil | VersaSil (Med4032) |
| | | NuSil | Optical Elastomers (LS-1200 and LS-3200/3300 series) |
| | | Artmolds.com | LifeRite Series |
| | | Artmolds.com | MoldRite Series (25) |
| | | Artmolds.com | SkinRite Series (10 |
| | | Renew | Silicone (00-30/50, 5, 10, 20 replicator) |
| | | Primasil | Sil 100 & 400 series |
| | | Alumilite | High Strength 2 & 3 |
| | | 3M | Impregum, Soft/DuoSoft Polyethers |
| | | 3M | Imprint 3, Express 2 VPS, (3M ESPE series) |
| | Urethane Rubber | Smooth on | Clear Flex 50 & 95 |
| | | Smooth on | Renew UR 40, 60, 80, 90 |

TABLE 2

Additives

| | | | |
|---|---|---|---|
| Foams | Rigid and Flexible Foam | Smooth on | Foam-it 3, 5, 8, 10, 15, 26 |
| | | Smooth on | Foam-iT III,, V, X, 17, 25 |
| | | Smooth on | Soma Foama-15 |
| | | Renew | Rigid Foam 10, Flexible foam 10, 25 |
| Additives | Silicone Rubber & Urethane | Smooth on | Ti-Vex Silicone Thickener |
| | | Smooth on | Silicone Thinner |
| | | Smooth on | Cryptolyte |

TABLE 2-continued

| | Additives | |
|---|---|---|
| Accessories | Smooth on | Slacker-deadener |
| | Smooth on | URE-FIL 9 |
| | Polytek | TinThix |
| | Polytek | PolyFiber II |
| | Polytek | Fumed Silica |
| | Polytek | Polyfil ND |
| | Artmolds.com | ThickRITE |
| Coloring | Smooth on | So-Strong Color Tints |
| | Smooth on | Ignite-Flourescent Pigments |
| | Smooth on | Sil-Pig-Silicone Pigments |
| | Artmolds.com | Cirius Paint Series |
| | Artmolds.com | Cirius Pigment Series |
| | NuSil | Med Series (4102, 4502, 4800, 4900) through Gayson Silicon Dispersions, Inc. (GSDI) |

To illustrate the methods and tissue models disclosed in the present application, a non-limiting list of example Embodiments is provided here:

Embodiment 1 can include subject matter (such as an apparatus, a device, a method, or one or more means for performing acts), such as can include a method of developing a tissue model. The subject matter can include determining material properties of a tissue, wherein the material properties include at least one of viscoelastic mechanical properties, electroconductive properties, anisotropic, thermoconductive properties, reflectivity, and color of the tissue, creating an anatomical structure of the tissue, and coupling an artificial tissue material to the anatomical structure, wherein the artificial tissue material has properties corresponding to the material properties of the tissue.

Embodiment 2 can include, or can optionally be combined with the subject matter of Embodiment 1, to optionally include the material properties being determined from a tissue database.

Embodiment 3 can include, or can optionally be combined with the subject matter of one or any combination of Embodiments 1 or 2, to optionally include the tissue database being a human tissue database.

Embodiment 4 can include, or can optionally be combined with the subject matter of one or any combination of Embodiments 1-3, to optionally include the human tissue database being generated by harvesting soft tissue specimens from a human, determining at least one of viscoelastic mechanical properties, electroconductive properties, and thermoconductive properties of the soft tissue, and stratifying data according to gender, age, and body mass index.

Embodiment 5 can include, or can optionally be combined with the subject matter of one or any combination of Embodiments 1-4, to optionally include the harvesting the soft tissue specimens from a human comprises harvesting the soft tissue within 24 hours of the death of a deceased human.

Embodiment 6 can include, or can optionally be combined with the subject matter of one or any combination of Embodiments 1-5, to optionally include the viscoelastic mechanical properties being determined by a uniaxial or a biaxial testing of the soft tissue.

Embodiment 7 can include, or can optionally be combined with the subject matter of one or any combination of Embodiments 1-6, to optionally include the creating of the anatomical structure comprising forming a three-dimensional model of the tissue.

Embodiment 8 can include, or can optionally be combined with the subject matter of one or any combination of Embodiments 1-7, to optionally include the forming of the three-dimensional model comprising three-dimensional printing of the three-dimensional model.

Embodiment 9 can include, or can optionally be combined with the subject matter of one or any combination of Embodiments 1-8, to optionally include the creating of the anatomical structure comprising casting the anatomical structure.

Embodiment 10 can include, or can optionally be combined with the subject matter of one or any combination of Embodiments 1-9, to optionally include the creating of the anatomical structure comprising collecting computer tomography or magnetic resonance imaging datasets of the tissue.

Embodiment 11 can include, or can optionally be combined with the subject matter of one or any combination of Embodiments 1-10, to optionally include the creating of the anatomical structure comprising processing at least one of computer tomography or magnetic resonance imaging images of the tissue through a composite software to generate imaging stack data, refining the stack data through image segmentation software, creating a virtual three-dimensional anatomical structure of the tissue based on the refined stack data, and printing the virtual three-dimensional anatomical structure using stereolithographic techniques to produce a three-dimensional printed model of the anatomical structure.

Embodiment 12 can include, or can optionally be combined with the subject matter of one or any combination of Embodiments 1-11, to optionally include the creating of the virtual three-dimensional anatomical structure comprising creating a coarse three-dimensional model of the anatomical structure based on the refined stack data, and refining the coarse three-dimensional model to generate the virtual three-dimensional anatomical structure of the tissue.

Embodiment 13 can include, or can optionally be combined with the subject matter of one or any combination of Embodiments 1-12, to optionally include the coupling of the artificial tissue material comprising applying a base material of the artificial tissue material on the anatomical structure.

Embodiment 14 can include, or can optionally be combined with the subject matter of one or any combination of Embodiments 1-13, to optionally include the applying of the base material comprising at least one of casting, machining or molding of the base material onto the anatomical structure.

Embodiment 15 can include, or can optionally be combined with the subject matter of one or any combination of Embodiments 1-14, to optionally include the base material being an organosilicate.

Embodiment 16 can include, or can optionally be combined with the subject matter of one or any combination of Embodiments 1-15, to optionally include the applying of the base material comprising applying a plurality of layers of the base material.

Embodiment 17 can include, or can optionally be combined with the subject matter of one or any combination of Embodiments 1-16, to optionally include applying an indicator material to the base material.

Embodiment 18 can include, or can optionally be combined with the subject matter of one or any combination of Embodiments 1-17, to optionally include the indicator material comprising an ultraviolet sensitive material.

Embodiment 19 can include, or can optionally be combined with the subject matter of one or any combination of Embodiments 1-18, to optionally include the ultraviolet sensitive material being transparent under normal light.

Embodiment 20 can include, or can optionally be combined with the subject matter of one or any combination of Embodiments 1-19, to optionally include the ultraviolet sensitive coating comprising at least one of a polyurethane or a silicone.

Embodiment 21 can include, or can optionally be combined with the subject matter of one or any combination of Embodiments 1-20, to optionally include the applying of the indicator material comprising applying the indicator material in at least one of a line, a dot or a pattern.

Embodiment 22 can include, or can optionally be combined with the subject matter of one or any combination of Embodiments 1-21, to optionally include positioning a sensor on or within at least one layer of the base material or between two or more layers of the base material.

Embodiment 23 can include, or can optionally be combined with the subject matter of one or any combination of Embodiments 1-22, to optionally include the sensor comprising at least one of a strain gauge, a capacitive diaphragm, an electromagnetic inductance diaphragm, an optical strain detection sensor, a potentiometer mechanism, a vibration sensor, an accelerometer, a dynamic switch element, a piezoelectric sensor, a flow sensor, and a leak testing pressure sensor.

Embodiment 24 can include, or can optionally be combined with the subject matter of one or any combination of Embodiments 1-23, to optionally include the sensor comprising a piezoresistive fabric, the piezoelectric fabric being capable of detecting deformation of the tissue model in response on contact with an object.

Embodiment 25 can include, or can optionally be combined with the subject matter of one or any combination of Embodiments 1-24, to optionally include the sensor being configured to measure tactile pressure on the tissue model with an object.

Embodiment 26 can include, or can optionally be combined with the subject matter of one or any combination of Embodiments 1-25, wherein the object is a surgical instrument or an organ.

Embodiment 27 can include, or can optionally be combined with the subject matter of one or any combination of Examples 1-26, to include subject matter (such as an apparatus, a device, a method, or one or more means for performing acts), such as can include a method of making an artificial tissue material. The subject matter can include adding an additive to an organo silicate material to form a mixture, and placing the mixture in a mold to form a molded sample.

Embodiment 28 can include, or can optionally be combined with the subject matter of one or any combination of Embodiments 1-27, to optionally include coating the molded sample with a talcum powder, and washing the sample with cold water to remove excess talcum powder.

Embodiment 29 can include, or can optionally be combined with the subject matter of one or any combination of Embodiments 1-28, to optionally include the adding of an additive comprising adding at least one of a silicone oil, petroleum jelly, glycerine, baby oil, talcum powder, a color, a tint, a dye, a metal wire, a dielectric wire, metal powders, a dielectric ink and a dielectric coating.

Embodiment 30 can include, or can optionally be combined with the subject matter of one or any combination of Examples 1-29, to include subject matter (such as an apparatus, a device, a method, or one or more means for performing acts), such as can include a tissue model. The subject matter can include a three-dimensional printed model, and an artificial tissue material coupled to the three-dimensional printed model, wherein the artificial tissue has properties corresponding to at least one of viscoelastic mechanical properties of a tissue, electroconductive properties of the tissue, and thermoconductive properties of the tissue.

Embodiment 31 can include, or can optionally be combined with the subject matter of one or any combination of Embodiments 1-30, to optionally include the artificial tissue material comprising an organosilicate base material.

Embodiment 32 can include, or can optionally be combined with the subject matter of one or any combination of Embodiments 1-31, to optionally include an indicator material applied to the organosilicate base material.

Embodiment 33 can include, or can optionally be combined with the subject matter of one or any combination of Embodiments 1-32, to optionally include the indicator material comprising an ultraviolet light sensitive material.

Embodiment 34 can include, or can optionally be combined with the subject matter of one or any combination of Embodiments 1-33, to optionally include the ultraviolet light sensitive material being transparent under normal light.

Embodiment 35 can include, or can optionally be combined with the subject matter of one or any combination of Embodiments 1-34, to optionally include the tissue comprising at least one of fat, connective tissues, nerve, artery, vein, muscle, tendon, ligaments, renal artery tissue, kidney tissue, ureter tissue, bladder tissue, prostate tissue, urethra tissue, bleeding aorta tissue, pyeloplasty tissue, Y/V plasty tissue, airway tissue, tongue tissue, complete hand tissue, general skin tissue, specific face skin tissue, eye tissue, brain tissue, vaginal wall, breast tissue, nasal tissue, cartilage, colon tissue, stomach tissue, liver tissue, rectum, and heart tissue, bowel tissue, pancreas tissue, gallbladder tissue, liver tissue, inferior vena cava, aorta, lung tissue, bronchial tissue, soft palate tissue, larynx tissue, pharynx tissue, epidermis tissue, dermis tissue, lip tissue, mucosal membrane tissue and adhesion tissue.

Embodiment 36 can include, or can optionally be combined with the subject matter of one or any combination of Embodiments 1-35, to optionally include at least one sensor configured to measure a deformation of the artificial tissue material.

Embodiment 37 can include, or can optionally be combined with the subject matter of one or any combination of Embodiments 1-36, to optionally include the at least one sensor comprising at least one of a strain gauge, a capacitive diaphragm, an electromagnetic inductance diaphragm, an optical strain detection sensor, a potentiometer mechanism, a vibration sensor, an accelerometer, a dynamic switch element, and a piezoelectric sensor.

Embodiment 38 can include, or can optionally be combined with the subject matter of one or any combination of Examples 1-37, to include subject matter (such as an apparatus, a device, a method, or one or more means for performing acts), such as can include a tissue model. The subject matter can include a three-dimensional printed model, an artificial tissue material coupled to the three-dimensional printed model, wherein the artificial tissue has properties corresponding to at least one of viscoelastic mechanical properties of a tissue, electroconductive properties of the tissue, and thermoconductive properties of the tissue, and an indicator material applied to the artificial tissue material.

Embodiment 39 can include, or can optionally be combined with the subject matter of one or any combination of Embodiments 1-38, to optionally include the indicator material comprising at least one of a photochromic material, a thermochromic material, a solvatochromic material, or a piezochromic material.

Embodiment 40 can include, or can optionally be combined with the subject matter of one or any combination of Embodiments 1-39, to optionally include the indicator material comprising a light-sensitive material that changes color under light having a first wavelength range.

Embodiment 41 can include, or can optionally be combined with the subject matter of one or any combination of Embodiments 1-40, to optionally include the light-sensitive material being transparent under light having a wavelength in a visible-light range.

Embodiment 42 can include, or can optionally be combined with the subject matter of one or any combination of Embodiments 1-41, to optionally include the first wavelength range being in an ultraviolet wavelength range.

Embodiment 43 can include, or can optionally be combined with the subject matter of one or any combination of Embodiments 1-42, to optionally include the indicator material being applied in a pattern configured to indicate or determine performance of a predetermined task.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A method of making a training model for training a medical or veterinary practitioner on performance of a medical or veterinary procedure, the method comprising:
   determining one or more first deformability properties of a soft tissue that is part of an anatomical system relevant to the procedure, the soft tissue having an anatomical structure within the relevant anatomical system, wherein the one or more first deformability properties include a Young's modulus of the soft tissue within the relevant anatomical system;
   selecting a composition of a silicone-based model material comprising an organosilicate material including a platinum-based silicone rubber or a tin-cured silicone rubber so that, when cured, the silicone-based model material will have one or more second deformability properties that are within 10% of the one or more first deformability properties of the soft tissue within the relevant anatomical system;
   applying the silicone-based model material onto a model support structure and thereby forming a tissue model having a geometry that corresponds to the anatomical structure of the soft tissue; and
   curing the applied silicone-based model material and thereby forming the training model such that the cured silicone-based model material has the geometry that corresponds to the anatomical structure of the soft tissue within the relevant anatomical system and such that the cured silicone-based model material has the one or more second deformability properties that are within 10% of the one or more first deformability properties of the soft tissue.

2. The method of claim 1, wherein the one or more first deformability properties of the soft tissue are determined from a tissue property database.

3. The method of claim 2, wherein the tissue property database is generated by:
   harvesting a soft tissue specimen from a human;
   measuring or calculating the one or more first deformability properties of the soft tissue specimen; and recording the measured or calculated one or more first deformability properties of the soft tissue specimen in the tissue property database.

4. The method of claim 1, further comprising creating the model support structure, wherein creating the model support structure comprises forming a three-dimensional structure of at least the portion of the relevant anatomical system.

5. The method of claim 1, further comprising applying an indicator material to the silicone-based model material.

6. The method of claim 5, wherein the indicator material comprises a light-sensitive material that changes color under light having a first wavelength.

7. The method of claim 6, wherein the light-sensitive material is transparent to light having a wavelength in a visible-light range.

8. The method of claim 6, wherein the first wavelength is in one of an ultraviolet wavelength range or an infrared wavelength range.

9. The method of claim 5, wherein applying the indicator material comprises applying the indicator material in a pattern.

10. The method of claim 1, further comprising positioning a sensor on or in the silicone-based model material, wherein the sensor comprises at least one of a strain gauge, a capacitive diaphragm, an electromagnetic inductance diaphragm, an optical strain detection sensor, a potentiometer mechanism, a vibration sensor, an accelerometer, a dynamic switch element, a piezoelectric sensor, a flow sensor, and a leak testing pressure sensor.

11. The method of claim 1, further comprising determining, in addition to the one or more first deformability properties of the soft tissue, one or more additional mechanical properties of the soft tissue, the one or more additional mechanical properties comprising at least one of viscoelasticity, yield stress, strain at yield, engineering stress, indentation, tear stress, strain rate insensitivity, and a portion of a stress-strain curve of the soft tissue, wherein the silicone-based model material further comprises one or more corresponding mechanical properties, and wherein the one or more corresponding mechanical properties are within 10% of the one or more additional mechanical properties of the soft tissue, wherein the one or more corresponding mechanical properties comprise at least one of viscoelasticity, yield stress, strain at yield, engineering stress, indentation, tear stress, strain rate insensitivity, and a portion of a stress-strain curve of the silicone-based model material.

12. The method of claim 1, further comprising:
determining one or more first optical properties of the soft tissue in addition to determining the one or more first deformability properties; and
wherein the composition of the silicone-based model material is selected so that the silicone-based model material includes one or more second optical properties that are within 10% of the one or more first optical properties of the soft tissue.

13. The method of claim 12, wherein the one or more first optical properties comprise at least one of reflectivity, light transmission of a selected range of wavelengths, and light absorption of a selected range of wavelengths by the soft tissue, and wherein the one or more second optical properties comprise at least of reflectivity, light transmission of a selected range of wavelengths, and light absorption of a selected range of wavelengths by the silicone-based model material.

14. The method of claim 12, further comprising:
determining a set of one or more additional material properties of the soft tissue in addition to determining the one or more first deformability properties and the one or more first optical properties, wherein the one or more additional material properties comprise at least one of an electroconductive property, a thermoconductive property, a chemical property, and an anisotropic property; and
wherein the selected silicone-based model material includes a set of one or more corresponding additional material properties that is within 10% of the set of one or more additional material properties of the soft tissue.

15. The method of claim 1, wherein applying the silicone-based model material to the model support structure comprises applying a plurality of layers of the silicone-based model material to the model support structure, and wherein curing the silicone-based model material comprises curing the applied layers of the silicone-based model material, wherein each of the plurality of layers of the cured silicone-based model material has a layer geometry that corresponds to a corresponding anatomical structure of a corresponding layer of the relevant anatomical structure of the soft tissue.

16. A training model for training a medical or veterinary practitioner on performance of a medical or veterinary procedure, the training model comprising:
a three-dimensional support structure; and
a silicone-based model material coupled to the three-dimensional support structure, the silicone-based model material comprising an organosilicate material including a platinum-based silicone rubber or a tin-cured silicone rubber, wherein the silicone-based model material has a geometry that corresponds to an anatomical structure of a corresponding soft tissue that is part of an anatomical system relevant to the procedure, wherein a composition of the silicone-based model material is selected to have one or more deformability properties, including a Young's modulus of the silicone-based model material, wherein the one or more deformability properties of the silicone-based model material are within 10% of one or more corresponding deformability properties of the corresponding soft tissue within the relevant anatomical system, the one or more corresponding deformability properties including a Young's modulus of the soft tissue within the relevant anatomical system.

17. The training model of claim 16, further comprising at least one sensor configured to measure a deformation of the silicone-based model material.

18. The training model of claim 16, further comprising an indicator material applied to the silicone-based model material.

19. The training model of claim 18, wherein the indicator material s applied in a pattern configured to indicate or determine performance of the procedure.

20. The training model of claim 18, wherein the indicator material comprises at least one of a photochromic material, a thermochromic material, a solvatochromic material, and a piezochromic material.

21. The training model of claim 18, wherein the indicator material comprises a light-sensitive material that changes color under light having a first wavelength.

22. The training model of claim 21, wherein the light-sensitive material is transparent to light having a wavelength in a visible-light range.

23. The training model of claim 21, wherein the first wavelength is in one of an ultraviolet wavelength range or an infrared wavelength range.

24. The training model of claim 16, wherein the one or more corresponding deformability properties of the corresponding soft tissue further comprise, in addition to the Young's modulus of the soft tissue, at least one of viscoelasticity, yield stress, strain at yield, engineering stress, indentation, tear stress, strain rate insensitivity, and a portion of a stress-strain curve of the soft tissue, and wherein the one or more selected deformability properties of the silicone-based model material comprise, in addition to the Young's modulus of the silicon-based model material, at least one of viscoelasticity, yield stress, strain at yield, engineering stress, indentation, tear stress, strain rate insensitivity, and a portion of a stress-strain curve of the silicone-based model material are within 10% of the one or more corresponding deformability properties of the soft tissue.

25. The training model of claim 16, wherein the silicone-based model material is further selected to have one or more optical properties that are within 10% of one or more corresponding optical properties of the corresponding soft tissue.

26. The training model of claim 25, wherein the one or more corresponding optical properties comprise at least one of reflectivity, light transmission of a selected range of wavelengths, and light absorption of a selected range of wavelengths by the corresponding soft tissue and the one or more optical properties of the silicon-based model material comprise at least of reflectivity, light transmission of a selected range of wavelengths, and light absorption of a selected range of wavelengths by the silicone-based model material.

27. The training model of claim 26, wherein the silicon-based model material is further selected to have a set of one or more additional material properties that are each within 10% for each of a corresponding set of one or more corresponding material properties of the corresponding soft tissue, in addition to the corresponding deformability properties and the corresponding optical properties, wherein the one or more additional material properties of the set comprise at least one of an electroconductive property, a thermoconductive property, a chemical property, and an anisotropic property.

28. A training model for training a medical or veterinary practitioner on performance of a medical or veterinary procedure, the training model comprising:
 a three-dimensional support structure; and
 a silicone-based model material coupled to the three-dimensional support structure, wherein the silicone-based model material has a geometry that corresponds to an anatomical structure of a corresponding soft tissue that is part of an anatomical system relevant to the procedure, wherein the anatomical structure of the corresponding soft tissue includes a plurality of at least three tissue layers,
 wherein the silicone-based model material coupled to the three-dimensional model structure comprises a plurality of at least three layers of the silicone-based model material, wherein each layer of the silicon-based model material has a layer geometry that corresponds to a corresponding anatomical structure of a corresponding one of the plurality of at least three tissue layers, and
 wherein a composition of the silicone-based model material of each of the plurality of at least three layers is selected to have one or more deformability properties, including a Young's modulus of the silicone-based model material, that are within 10% of one or more corresponding deformability, properties of the corresponding one of the plurality of at least three tissue layers, the one or more corresponding deformability properties including a Young's modulus of the soft tissue at the corresponding one of the plurality of at least three tissue layers.

29. The training model of claim 28, wherein the one or more corresponding deformability properties of the corresponding one of the plurality of at least three tissue layers include, in addition to Young's modulus of the corresponding one of the plurality of at least three tissue layers, at least one of viscoelasticity, yield stress, strain at yield, engineering stress, indentation, tear stress, strain rate insensitivity, and a portion of a stress-strain curve of the corresponding one of the plurality of at least three tissue layers, and wherein the one or more selected deformability properties of the silicone-based model material of each of the plurality of at least three layers of the silicone-based model material comprise, in addition to the Young's modulus of the silicon-based model material, at least one of viscoelasticity, yield stress, strain at yield, engineering stress, indentation, tear stress, strain rate insensitivity, and a portion of a stress-strain curve of the silicone-based model material, and wherein the one or more selected deformability properties of the silicone-based model material of each of the plurality of at least three layers of the silicone-based model material are within 10% of the one or more corresponding deformability properties of the corresponding one of the plurality of at least three tissue layers.

30. The raining model of claim 28, wherein the silicone-based model material comprises an organosilicate material.

* * * * *

UNITED STATES PATENT AND TRADEMARK OFFICE
CERTIFICATE OF CORRECTION

PATENT NO. : 9,805,624 B2
APPLICATION NO. : 13/630715
DATED : October 31, 2017
INVENTOR(S) : Reihsen et al.

It is certified that error appears in the above-identified patent and that said Letters Patent is hereby corrected as shown below:

In the Specification

In Column 1, Line 65, delete "organo silicate" and insert --organosilicate-- therefor In Column 5, Line 46, delete "organo silicate" and insert --organosilicate-- therefor In Column 7, Line 42, delete "organo silicate" and insert --organosilicate-- therefor In Column 7, Line 47, delete "organo silicate" and insert --organosilicate-- therefor In Column 7, Line 49, delete "organo silicate" and insert --organosilicate-- therefor In Column 7, Line 50, delete "organo silicate" and insert --organosilicate-- therefor In Column 7, Line 56, delete "organo silicate" and insert --organosilicate-- therefor In Column 8, Line 58, delete "organo silicate" and insert --organosilicate-- therefor In Column 8, Line 58, delete "organo silicate" and insert --organosilicate-- therefor In Column 8, Line 61, delete "organo silicate" and insert --organosilicate-- therefor In Column 9, Line 12, delete "organo silicate" and insert --organosilicate-- therefor In Column 10, Line 31, delete "organo silicate" and insert --organosilicate-- therefor In Column 10, Lines 64-65, delete "piezoeelectric" and insert --piezoelectric-- therefor In Column 12, Line 65, delete "organo silicate" and insert --organosilicate-- therefor Signed and Sealed this
Fourteenth Day of May, 2019

Andrei Iancu
*Director of the United States Patent and Trademark Office*

CERTIFICATE OF CORRECTION (continued)
U.S. Pat. No. 9,805,624 B2

In Column 13, Line 9, delete "organo silicate" and insert --organosilicate-- therefor In Column 13, Line 35, delete "granulo sum," and insert --granulosum,-- therefor In Column 13, Line 41, delete "organo silicate" and insert --organosilicate-- therefor In Column 17, Line 44, delete "organo silicate" and insert --organosilicate-- therefor In the Claims In Column 22, Line 51, in Claim 19, delete "s" and insert --is-- therefor In Column 24, Line 16, in Claim 28, delete "deformability," and insert --deformability-- therefor In Column 24, Line 45, in Claim 30, delete "raining" and insert --training-- therefor